(12) United States Patent
Miller et al.

(10) Patent No.: US 9,329,185 B2
(45) Date of Patent: May 3, 2016

(54) SULFONATE COMPOUNDS

(71) Applicant: University of Massachusetts, Boston, MA (US)

(72) Inventors: Stephen C. Miller, Cambridge, MA (US); Steven M. Pauff, Worcester, MA (US); Adam Choi, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/202,211

(22) Filed: Mar. 10, 2014

(65) Prior Publication Data

US 2014/0275526 A1 Sep. 18, 2014

Related U.S. Application Data

(60) Provisional application No. 61/800,613, filed on Mar. 15, 2013.

(51) Int. Cl.
*G01N 33/58* (2006.01)
*C07C 1/00* (2006.01)

(52) U.S. Cl.
CPC ............. *G01N 33/582* (2013.01); *C07C 1/00* (2013.01)

(58) Field of Classification Search
None
See application file for complete search history.

(56) References Cited

PUBLICATIONS

Miller, S., 74(13) J.O.C. 4632-4635 (2010) (CAS Abstract).*
Callander et al., 22(2) Tetrahedron 419-52 (1966) (CAS Abstract).*
DePuy et al., 39(7) J.O.C. 878-81 (1974) (CAS Abstract).*
Pauff & Miller, 78(2) J.O.C. 711-716 (2013).*
Allen et al., 105(8) J. Am. Chem. Soc. 2343-50 (1983) (CAS Abstract).*
Richard, J., 23 J.O.C., Chem. Commc'ns. 1768-9 (1987) (CAS Abstract).*
Murata et al., 16(2) Memoirs of the Faculty of Sci., Kyushu Univ. Series C: Chem. 243-56 (1988) (CAS Abstract).*
Rusha, Laert et al., "Design and application of esterase-labile sulfonate protecting groups", Chem. Commun., vol. 47:2038-2040, 2011.
Pauff, Steven M. et al., "A Trifluoroacetic Acid-labile Sulfonate Protecting Group and Its Use in the Synthesis of a Near-IR Fluorophore", J. Org. Chem., vol. 78:711-716, 2013.
Pauff, Steven M. et al., "Synthesis of Near-IR Fluorescent Oxazine Dyes with Esterase-Labile Sulfonate Esters", Organic Letters, vol. 13:6196-6199, 2011.

* cited by examiner

*Primary Examiner* — Timothy R Rozof
(74) *Attorney, Agent, or Firm* — Fish & Richardson P.C.

(57) ABSTRACT

This disclosure relates to compounds containing a fluorophore covalently bonded to at least one protected sulfonate group of formula (I):

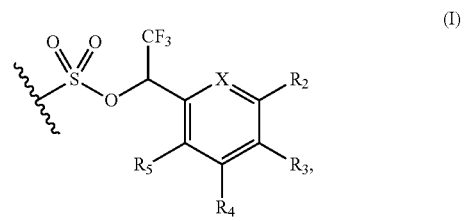

in which X and $R_2$-$R_5$ are defined in the specification. This disclosure also relates to use of these compounds as dyes in an imaging methods, as well as intermediates that can be used to prepare these compounds.

24 Claims, No Drawings

SULFONATE COMPOUNDS

CROSS-REFERENCE TO RELATED APPLICATION

This application claims priority to U.S. Provisional Application No. 61/800,613, filed on Mar. 15, 2013, the contents of which are hereby incorporated by reference in their entirety.

STATEMENT REGARDING FEDERALLY SPONSORED RESEARCH

This invention was made with government support under grant no. GM087460 awarded by the National Institutes of Health. The government has certain rights in the invention.

TECHNICAL FIELD

This invention relates to sulfonate compounds, as well as related imaging methods and intermediates.

BACKGROUND

Sulfonates are widely used to impart water-solubility to hydrophobic molecules. However, the high polarity of the sulfonate groups in sulfonated molecules dominates their physical properties and precludes their ability to diffuse across cellular membranes. Thus, many sulfonated fluorescent dyes and potential therapeutic molecules cannot access intracellular locations. Furthermore, there are few useful protecting groups or prodrugs for sulfonates, as most sulfonate esters are highly reactive with nucleophiles, and those that are stable generally require harsh conditions for removal.

SUMMARY

This disclosure is based on the unexpected discovery that certain protected sulfonated fluorescent dyes can readily diffuse across cellular membranes and can be deprotected in an intracellular environment (e.g., by an enzyme or reductive conditions in the intracellular environment), thereby allowing delivery of polar sulfonate fluorescent dyes into live cells (e.g., the cytoplasm of live cells).

In one aspect, this disclosure features sulfonate compounds containing a fluorophore covalently bonded to at least one protected sulfonate group of formula (I):

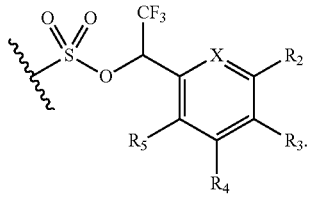

In formula (I), X is $C(R_1)$ or N, in which $R_1$ is H, halo, or $C_1$-$C_{10}$ alkyl; $R_3$ is H, S—S—$R_a$, S—$R_a$, $NO_2$, $OR_a$, $OC(O)R_a$, halo, $C_1$-$C_{10}$ alkyl, or aryl, in which $R_a$ is $C_1$-$C_{10}$ alkoxy, $C_1$-$C_{10}$ alkyl, or $C_1$-$C_{20}$ heterocycloalkyl; and each of $R_2$, $R_4$, and $R_5$, independently, is H, halo, or $C_1$-$C_{10}$ alkyl; provided that, when X is CH, $R_3$ is not $OC(O)CH_3$.

In another aspect, this disclosure features imaging methods that include delivering one or more of the sulfonate compounds described above into a cell; and irradiating the cell with an excitation light, thereby generating fluorescence from the cell.

In still another aspect, this disclosure features intermediate compounds of formula (IV):

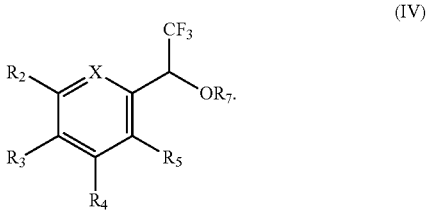

In formula (IV), X is $C(R_1)$ or N, in which $R_1$ is H, halo, or $C_1$-$C_{10}$ alkyl; $R_3$ is H, S—S—$R_a$, S—$R_a$, $NO_2$, $OR_a$, $OC(O)R_a$, halo, $C_1$-$C_{10}$ alkyl, or aryl, in which $R_a$ is $C_1$-$C_{10}$ alkoxy, $C_1$-$C_{10}$ alkyl, or $C_1$-$C_{20}$ heterocycloalkyl; each of $R_2$, $R_4$, and $R_5$, independently, is H, halo, or $C_1$-$C_{10}$ alkyl; and $R_7$ is H, $OS(O)_2(CH_2)_m R_d$, or $Si(R_e R_f R_g)$, in which m is 1, 2, 3, 4, 5, or 6, $R_d$ is a leaving group (e.g., halo, tosylate, mesylate, or triflate), and each of $R_e$, $R_f$, and $R_g$, independently, is $C_1$-$C_{10}$ alkyl; provided that, when X is CH and $R_7$ is H, $R_3$ is not H, halo, $NO_2$, $C_1$-$C_{10}$ alkyl, or $OC(O)CH_3$, and when X is CH and $R_7$ is $OS(O)_2(CH_2)_3Cl$ or $OS(O)_2(CH_2)_3I$, $R_3$ is not H or $OC(O)CH_3$. These intermediate compounds can be used to prepare the compounds of formula (I).

Other features, objects, and advantages will be apparent from the description, drawings, and claims.

DETAILED DESCRIPTION

In general, this disclosure relates to sulfonate compounds (e.g., protected sulfonated fluorescent dyes), as well as related imaging methods and intermediates.

Sulfonate Compounds

In some embodiments, this disclosure relates to sulfonate compounds of containing a fluorophore covalently bonded to at least one protected sulfonate group of formula (I):

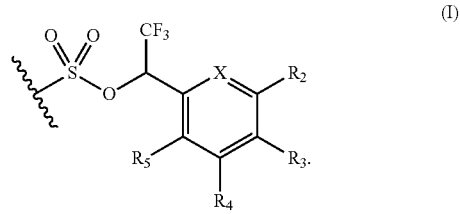

In formula (I), X is $C(R_1)$ or N, in which $R_1$ is H, halo, or $C_1$-$C_{10}$ alkyl; $R_3$ is H, S—S—$R_a$, S—$R_a$, $NO_2$, $OR_a$, $OC(O)R_a$, halo, $C_1$-$C_{10}$ alkyl, or aryl, in which $R_a$ is $C_1$-$C_{10}$ alkoxy, $C_1$-$C_{10}$ alkyl, or $C_1$-$C_{20}$ heterocycloalkyl; and each of $R_2$, $R_4$, and $R_5$, independently, is H, halo, or $C_1$-$C_{10}$ alkyl; provided that, when X is CH, $R_3$ is not $OC(O)CH_3$. As used herein, the term "fluorophore" refers to a fluorescent moiety (i.e., a group which can emit light upon light excitation).

The term "alkyl" refers to a saturated, linear or branched hydrocarbon moiety, such as —$CH_3$ or —$CH(CH_3)_2$. The term "alkoxy" refers to a saturated, linear or branched hydrocarbon moiety containing an oxygen atom, such as —$OCH_3$ or —$OCH(CH_3)_2$. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. As used herein, the term "heterocycloalkyl" refers to a saturated, cyclic moiety having at least one ring heteroatom (e.g., N, O, or S), such as 4-tetrahydropyranyl. Alkyl, aryl and heterocycloalkyl mentioned herein include both substituted and unsubstituted moieties, unless specified otherwise. Possible substituents on aryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl include all of the above-recited substituents except $C_1$-$C_{10}$ alkyl. Aryl and heterocycloalkyl also include moieties in which at least one aromatic ring is fused with one or more other rings (e.g., 5-7 membered rings, aromatic or non-aromatic, optionally containing a heteroatom such as N, O, or S).

Referring to formula (I), a subset of the at least one protected sulfonate group described above are those in which $R_3$ is S—S—$R_a$ or $NO_2$. For example, $R_a$ can be $C_1$-$C_{10}$ alkyl (e.g., $CH_3$ or $CH_2CH_3$) optionally substituted with NRR', each of R and R', independently, being H or $C_1$-$C_{10}$ alkyl (e.g., $CH_3$). In other words, $R_3$ can be S—S—$CH_3$ or S—S—$CH_2CH_2N(CH_3)_2$. In these compounds, X can be $C(R_1)$, in which $R_1$ can be H or F; and each of $R_2$, $R_4$, and $R_5$ can be H. Without wishing to be bound by theory, it is believed that, when $R_3$ is S—S—$R_a$ or $NO_2$, the at least one protected sulfonate group of formula (I) can be deprotected under reducing conditions (such as those found in a live cell) or by a reductase to form a $SO_3H$ group. Further, without wishing to be bound by theory, it is believed that a fluorescent dye having the protected sulfonate group of formula (I) can readily diffuse across cellular membranes and can be deprotected in an intracellular environment (e.g., by an enzyme or reductive conditions in the intracellular environment), thereby allowing delivery of a polar sulfonate fluorescent dye into the cytoplasm of live cells. By contrast, a conventional hydrophilic sulfonate fluorescent dye cannot easily diffuse across cellular membranes to enter into live cells and a conventional hydrophobic sulfonate fluorescent dye is typically retained by cell membranes or cell organelles, but not by cell cytoplasm.

Referring to formula (I), another subset of the least one protected sulfonate group described above are those in which $R_3$ is H, halo (e.g., F, Cl, or Br), $C_1$-$C_{10}$ alkyl (e.g., methyl or isopropyl), or aryl (e.g., phenyl). In these compounds, X can be $C(R_1)$, in which $R_1$ can be H or F; $R_5$ can be H or F; and each of $R_2$ and $R_4$ can be H. Without wishing to be bound by theory, it is believed that, when $R_3$ is H, halo, $C_1$-$C_{10}$ alkyl, or aryl, the at least one protected sulfonate group of formula (I) can be deprotected under acidic conditions (e.g., in the presence of trifluoroacetic acid) to form a $SO_3H$ group. In addition, without wishing to be bound by theory, it is believed that protecting a sulfonate group by a group that can be deprotected under acidic conditions can facilitate purification of a sulfonate compound. For example, a sulfonated near-IR dye (e.g., an oxazine containing sulfonic acid groups) may require use of HPLC for its purification due to its high polarity. However, it has been surprisingly found that a sulfonated dye protected by an acid-labile group can allow the dye to be soluble in organic solvents and to be purified by a silica gel flash chromatography (a much easier purification method than HPLC). The purified protected sulfonate dye can then be deprotected to provide the desired sulfonated near-IR dye.

Referring to formula (I), another subset of the least one protected sulfonate group described above are those in which $R_3$ is $OC(O)R_a$, in which $R_a$ is $C_1$-$C_{10}$ alkyl (e.g., $CH_3$) optionally substituted with halo (e.g., F, Cl, or Br), OR, $C_3$-$C_{20}$ cycloalkyl, $C_1$-$C_{20}$ heterocycloalkyl (e.g.,

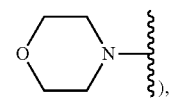

aryl (e.g., phenyl), or heteroaryl, R being H or $C_1$-$C_{10}$ alkyl (e.g., $CH_3$). In these compounds, X can be $C(R_1)$ or N, in which $R_1$ is H; and each of $R_2$, $R_4$, and $R_5$ can be H. Without wishing to be bound by theory, it is believed that, when $R_3$ is $OC(O)R_a$, the at least one protected sulfonate group of formula (I) can be deprotected by an esterase (e.g., an esterase found in a live cell) to form a $SO_3H$ group.

Referring to formula (I), the fluorophore can include a naphthalene moiety, a cyanine moiety, an oxazine moiety, a coumarin moiety, a rhodamine moiety, or a xanthene moiety, each of which can be optionally substituted with $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, $OR_b$, $SR_b$, $NR_bR_c$, $COOR_b$, or $COR_b$, each $R_b$ and $R_c$, independently, being H or $C_1$-$C_{10}$ alkyl. For example, the fluorophore can include a moiety selected from the group consisting of:

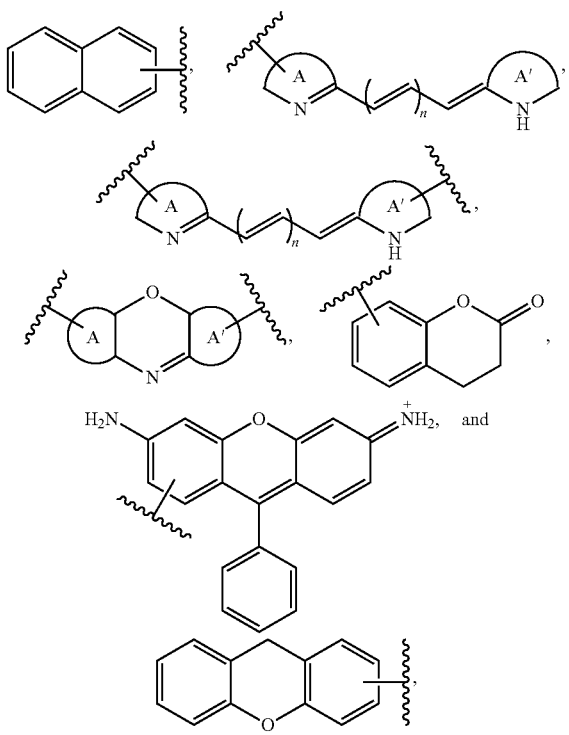

in which n is 1, 2, or 3, each of A and A', independently, is a 5-7 membered ring optionally fused with at least one 5-7 membered ring, and each moiety is optionally substituted with $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, $OR_b$, $SR_b$, $NR_bR_c$, $COOR_b$, or $COR_b$, each $R_b$ and $R_c$, independently, being H or $C_1$-$C_{10}$ alkyl. Exemplary fluorophores include:

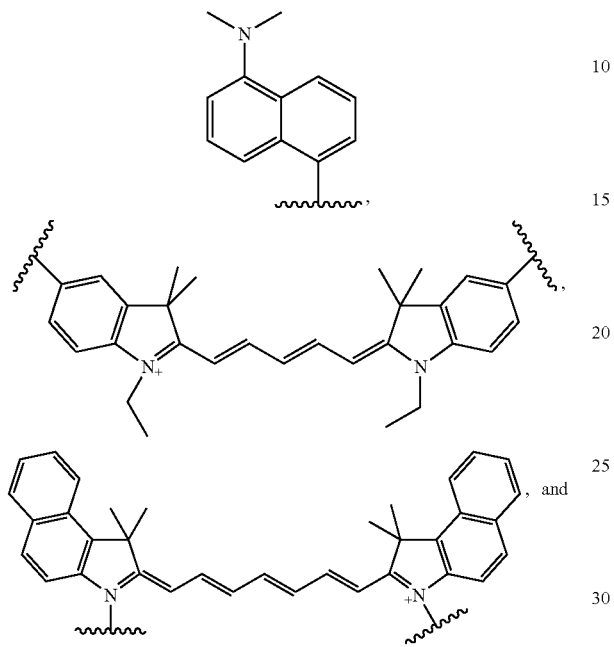

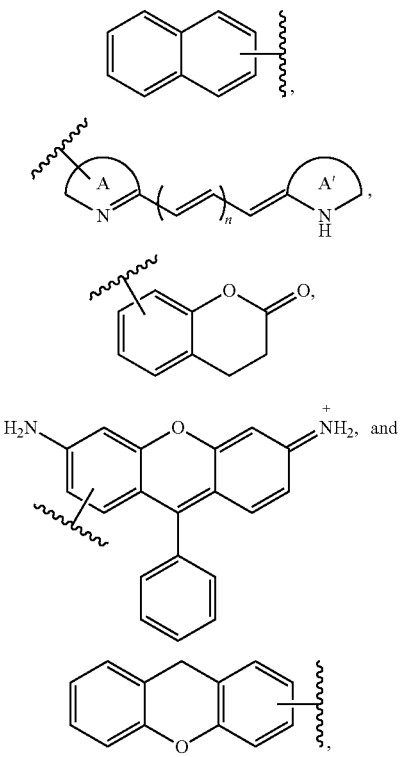

In some embodiments, the sulfonate compounds described above can be of formula (II):

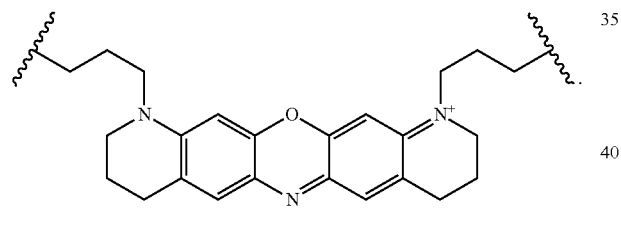

In formula (II), X is $C(R_1)$ or N, in which $R_1$ is H, halo, or $C_1$-$C_{10}$ alkyl; $R_3$ is H, S—S—$R_a$, S—$R_a$, $NO_2$, $OR_a$, $OC(O)R_a$, halo, $C_1$-$C_{10}$ alkyl, or aryl, in which $R_a$ is $C_1$-$C_{10}$ alkoxy, $C_1$-$C_{10}$ alkyl, or $C_1$-$C_{20}$ heterocycloalkyl; each of $R_2$, $R_4$, and $R_5$, independently, is H, halo, or $C_1$-$C_{10}$ alkyl; and $R_6$ is a fluorophore; provided that, when X is CH, $R_3$ is not $OC(O)CH_3$. For example, $R_6$ can be a fluorophore selected from the group consisting of:

in which n, A, and A' are defined above. An exemplary fluorophore for $R_6$ is

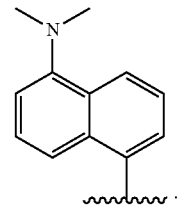 [SMILES: *c1cccc2c(N(C)C)cccc12]

Referring to formula (II), a subset of sulfonate compounds can be those in which $R_3$ is S—S—$R_a$ or $NO_2$. For example, $R_a$ can be $C_1$-$C_{10}$ alkyl (e.g., $CH_3$ or $CH_2CH_3$) optionally substituted with NRR', each of R and R', independently, being H or $C_1$-$C_{10}$ alkyl (e.g., $CH_3$). In other words, $R_3$ can be S—S—$CH_3$ or S—S—$CH_2CH_2N(CH_3)_2$. In these compounds, X can be $C(R_1)$, in which $R_1$ can be H or F; and each of $R_2$, $R_4$, and $R_5$ can be H. Examples of such sulfonate compounds include Compounds 1 and 2 below:

Compound 1

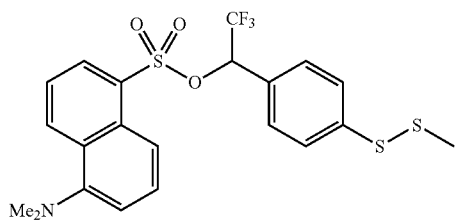

Compound 2

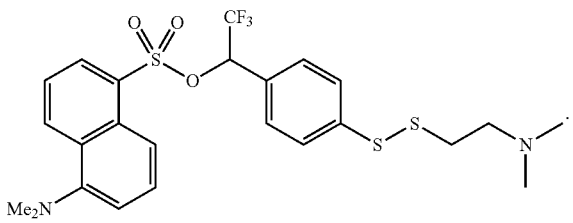

Referring to formula (II), another subset of sulfonate compounds can be those in which $R_3$ is H, halo (e.g., F, Cl, or Br), $C_1$-$C_{10}$ alkyl (e.g., methyl or isopropyl), or aryl (e.g., phenyl). In these compounds, X can be $C(R_1)$, in which $R_1$ can be H or F; $R_5$ can be H or F; and each of $R_2$ and $R_4$ can be H. Examples of such sulfonate compounds include Compounds 3-8, 26, and 27 below:

Compound 3

Compound 4

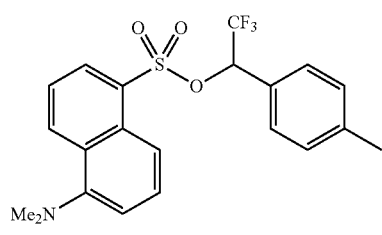

Compound 5

Compound 6

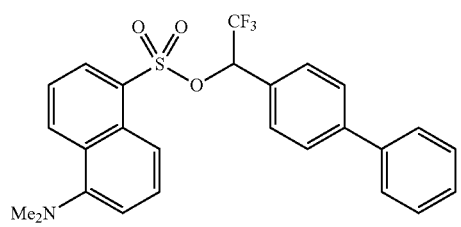

Compound 7

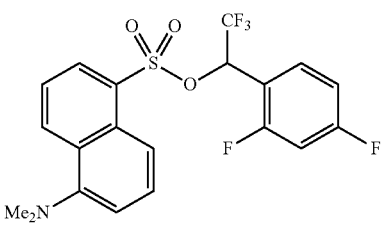

Compound 8

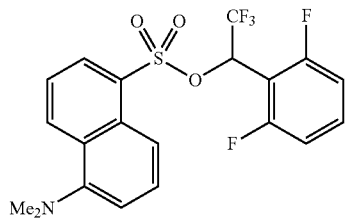

Compound 26

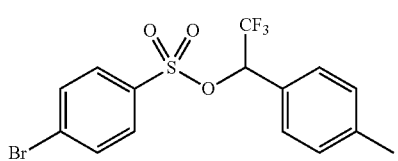

Compound 27

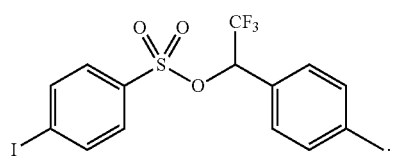

Referring to formula (II), another subset of sulfonate compounds can be those in which $R_3$ is $OC(O)R_a$, in which $R_a$ is $C_1$-$C_{10}$ alkoxy (e.g., ethoxy) or $C_1$-$C_{10}$ alkyl (e.g., $CH_3$) optionally substituted with halo (e.g., F, Cl, or Br), OR, $C_3$-$C_{20}$ cycloalkyl, $C_1$-$C_{20}$ heterocycloalkyl (e.g.,

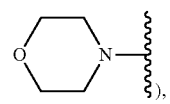

), aryl (e.g., phenyl), or heteroaryl, R being H or $C_1$-$C_{10}$ alkyl (e.g., $CH_3$). In these compounds, X can be $C(R_1)$ or N, in which $R_1$ is H; and each of $R_2$, $R_4$, and $R_5$ can be H. Examples of such sulfonate compounds include Compounds 9-12 and 28 below:

Compound 9

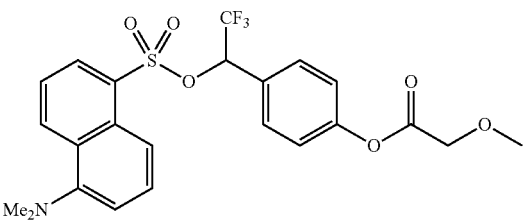

Compound 10

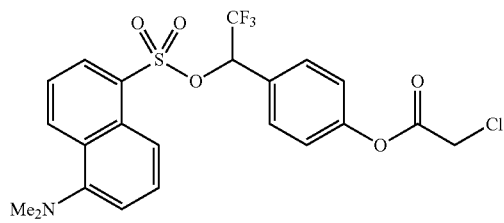

Compound 11

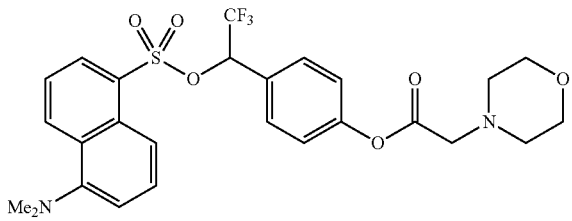

Compound 12

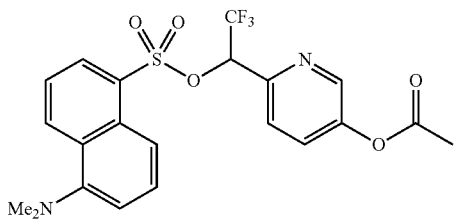

Compound 28

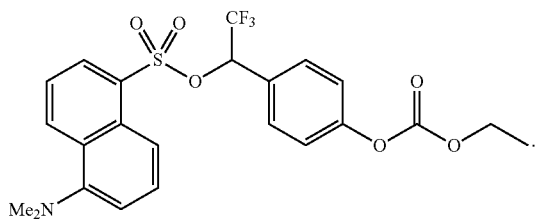

In some embodiments, the sulfonate compounds described above can be of formula (III):

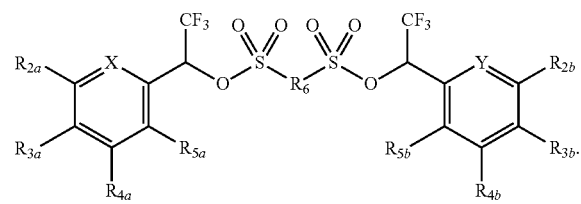

(III)

In formula (III), X is $C(R_{1a})$ or N, in which $R_{1a}$ is H, halo, or $C_1$-$C_{10}$ alkyl; Y is $C(R_{1b})$ or N, in which $R_{1b}$ is H, halo, or $C_1$-$C_{10}$ alkyl; each of $R_{3a}$ and $R_{3b}$, independently, is H, S—S—$R_a$, S—$R_a$, $NO_2$, $OR_a$, $OC(O)R_a$, halo, $C_1$-$C_{10}$ alkyl, or aryl, in which $R_a$ is $C_1$-$C_{10}$ alkoxy, $C_1$-$C_{10}$ alkyl, or $C_1$-$C_{20}$ heterocycloalkyl; each of $R_{2a}$, $R_{2b}$, $R_{4a}$, $R_{4b}$, $R_{5a}$, and $R_{5b}$, independently, is H, halo, or $C_1$-$C_{10}$ alkyl; and $R_6$ is a fluorophore; provided that, when X is CH and Y is CH, each of $R_{3a}$ and $R_{3b}$ is not $OC(O)CH_3$. For example, $R_6$ can be a fluorophore selected from the group consisting of:

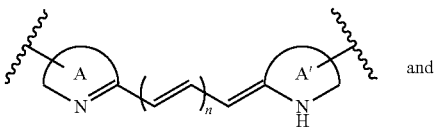 and

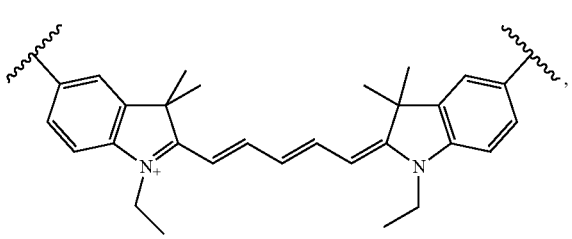

in which n, A, and A' are defined above. Exemplary fluorophores for $R_6$ include

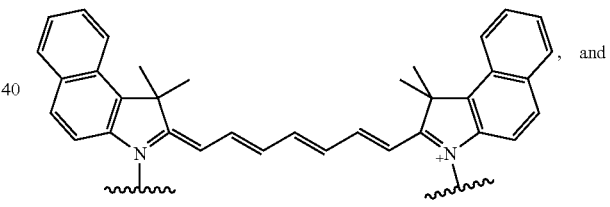

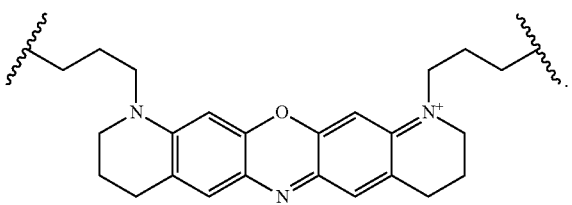, and

.

Referring to formula (III), a subset of sulfonate compounds can be those in which each of $R_{3a}$ and $R_{3b}$, independently, is S—S—$R_a$ or $NO_2$, in which $R_a$ is $C_1$-$C_{10}$ alkyl (e.g., $CH_3$ or $CH_2CH_3$) optionally substituted with NRR', each of R and R', independently, being H or $C_1$-$C_{10}$ alkyl (e.g., $CH_3$). In other words, each of $R_{3a}$ and $R_{3b}$, independently, can be S—S—$CH_3$ or S—S—$CH_2CH_2N(CH_3)_2$. In these compounds, X can be $C(R_{1a})$ and Y can be $C(R_{1b})$, in which each of $R_{1a}$ and $R_{1b}$, independently, can be H or F; and each of $R_{2a}$, $R_{2b}$, $R_{4a}$, $R_{4b}$, $R_{5a}$, and $R_{5b}$ can be H. Examples of such sulfonate compounds include Compound 24 and 25 below:

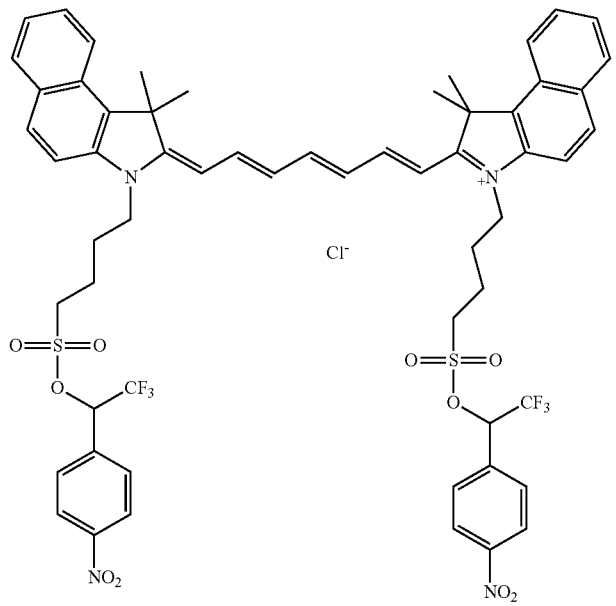

Compound 24

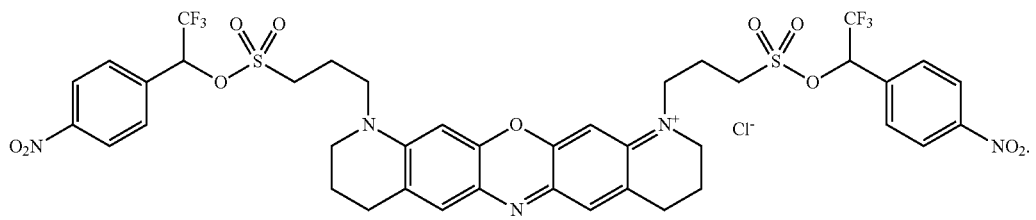

Compound 25

Referring to formula (III), another subset of sulfonate compounds can be those in which each of $R_{3a}$ and $R_{3b}$, independently, is H, halo (e.g., F, Cl, or Br), $C_1$-$C_{10}$ alkyl (e.g., methyl or isopropyl), or aryl (e.g., phenyl). In these compounds, X can be $C(R_{1a})$ and Y can be $C(R_{1b})$, in which each of $R_{1a}$ and $R_{1b}$, independently, can be H or F; each of $R_{5a}$ and $R_{5b}$, independently, can be H or F; and each of $R_{2a}$, $R_{2b}$, $R_{4a}$, and $R_{4b}$ can be H. Examples of such sulfonate compounds include Compound 13 and 34 below:

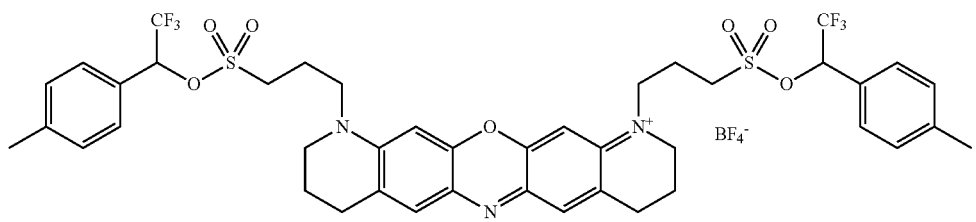

Compound 13

Compound 34

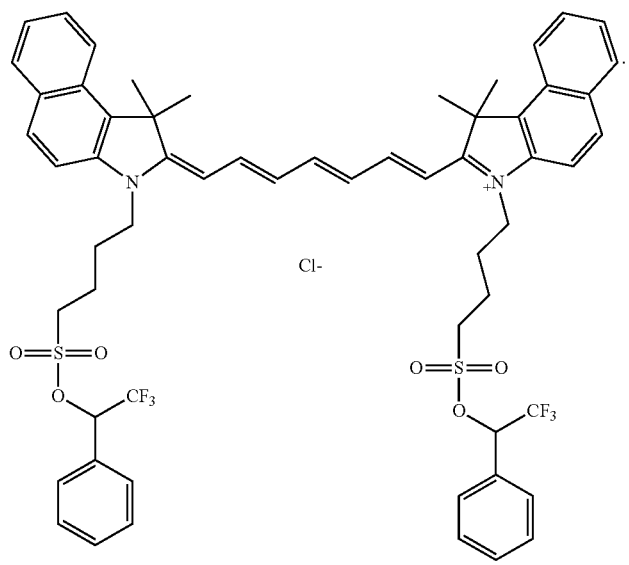

Referring to formula (III), another subset of sulfonate compounds can be those in which each of $R_{3a}$ and $R_{3b}$, independently, is $OC(O)R_a$, in which $R_a$ is $C_1$-$C_{10}$ alkyl (e.g., $CH_3$) optionally substituted with halo (e.g., F, Cl, or Br), OR, $C_3$-$C_{20}$ cycloalkyl, $C_1$-$C_{20}$ heterocycloalkyl (e.g.,

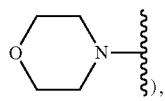

aryl (e.g., phenyl), or heteroaryl, R being H or $C_1$-$C_{10}$ alkyl (e.g., $CH_3$). In these compounds, X can be $C(R_{1a})$ or N and Y can be $C(R_{1b})$ or N, in which each of $R_{1a}$ and $R_{1b}$ can be H; and each of $R_{2a}$, $R_{2b}$, $R_{4a}$, $R_{4b}$, $R_{5a}$, and $R_{5b}$ can be H. Examples of such sulfonate compounds include Compounds 14 and 35 below:

Compound 14

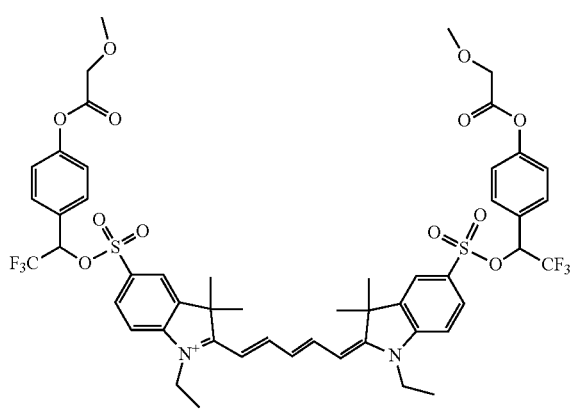

Compound 35

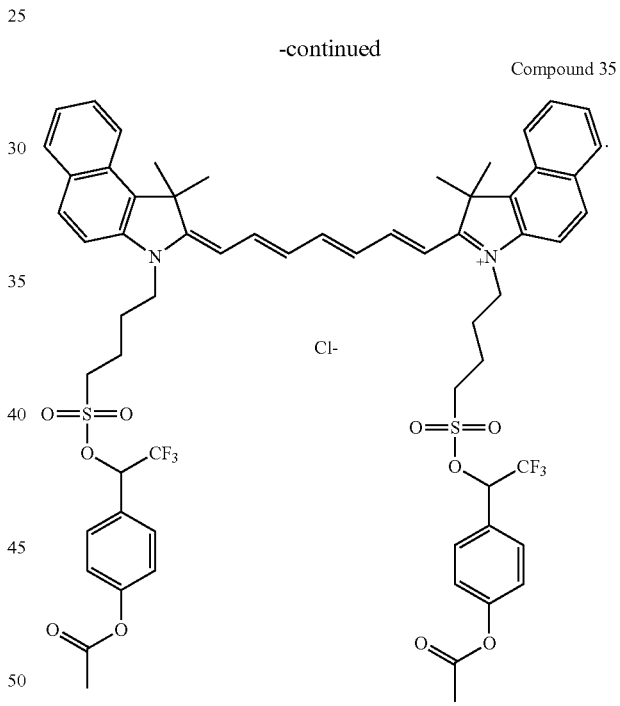

The sulfonate compounds described herein include the compounds themselves, as well as their salts, precursors, and solvates, if applicable. A salt, for example, can be formed between an anion and a positively charged group (e.g., amino) on a sulfonate compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a sulfonate compound. Suitable cations include sodium ion, potassium ion, magnesium ion, calcium ion, and an ammonium cation such as tetramethylammonium ion. The sulfonate compounds also include those salts containing quaternary nitrogen atoms. Examples of precursors include esters, amides, carbamates, carbonates, and other pharmaceutically acceptable derivatives, which, upon administration to a subject, are capable of providing active sulfonate compounds. A solvate refers to a complex formed between an active sulfonate compound and a pharmaceutically acceptable solvent. Examples of pharmaceutically acceptable solvents include water, ethanol, isopropanol, ethyl acetate, acetic acid, and ethanolamine.

Also within the scope of this disclosure is a pharmaceutical composition containing an effective amount of at least one sulfonate compound described above and a pharmaceutical acceptable carrier.

The sulfonate compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Intermediate Compounds

In some embodiments, this disclosure relates to intermediate compounds that can be used to prepare the sulfonate compounds described herein. In some embodiments, the intermediate compounds can be of formula (IV):

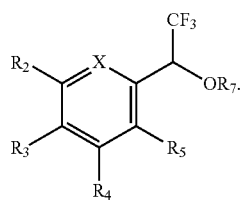

(IV)

In formula (IV), X is $C(R_1)$ or N, in which $R_1$ is H, halo, or $C_1$-$C_{10}$ alkyl; $R_3$ is H, S—S—$R_a$, S—$R_a$, $NO_2$, $OR_a$, $OC(O)R_a$, halo, $C_1$-$C_{10}$ alkyl, or aryl, in which $R_a$ is $C_1$-$C_{10}$ alkyl or $C_1$-$C_{20}$ heterocycloalkyl; and each of $R_2$, $R_4$, and $R_5$, independently, is H, halo, or $C_1$-$C_{10}$ alkyl; and $R_7$ is H, $OS(O)_2(CH_2)_mR_d$, or $Si(R_eR_fR_g)$, in which m is 1, 2, 3, 4, 5, or 6, $R_d$ is a leaving group (e.g., halo, tosylate, mesylate, or triflate), and each of $R_e$, $R_f$, and $R_g$, independently, is $C_1$-$C_{10}$ alkyl; provided that, when X is CH and $R_7$ is H, $R_3$ is not H, halo, $NO_2$, $C_1$-$C_{10}$ alkyl, or $OC(O)CH_3$, and when X is CH and $R_7$ is $OS(O)_2(CH_2)_3Cl$ or $OS(O)_2(CH_2)_3I$, $R_3$ is not H or $OC(O)CH_3$.

Referring to formula (IV), a subset of intermediate compounds includes those in which $R_7$ is H. In some of these compounds, when X is $C(R_1)$ (in which $R_1$ can be H), $R_3$ can be S—S—$R_a$ or S—$R_a$, in which $R_a$ is $C_1$-$C_{20}$ heterocycloalkyl or $C_1$-$C_{10}$ alkyl (e.g., $CH_3$ or $CH_2CH_3$) optionally substituted with NRR', each of R and R', independently being H or $C_1$-$C_{10}$ alkyl (e.g., $CH_3$); and each of $R_2$, $R_4$, and $R_5$ can be H. In some of these compounds, when X is $C(R_1)$ in which $R_1$ can be H), $R_3$ can be aryl (e.g., phenyl); and each of $R_2$, $R_4$, and $R_5$ can be H. In some of these compounds, when X is $C(R_1)$ (in which $R_1$ can be H), $R_3$ can be $OC(O)R_a$, in which $R_a$ can be $C_1$-$C_{10}$ alkyl substituted with halo (F, Cl, or Br), OR, $C_3$-$C_{20}$ cycloalkyl, $C_1$-$C_{20}$ heterocycloalkyl (e.g.,

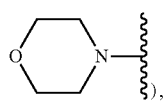

), aryl (e.g., phenyl), or heteroaryl, R being H or $C_1$-$C_{10}$ alkyl (e.g., $CH_3$); and each of $R_2$, $R_4$, and $R_5$ can be H. Examples of such intermediate compounds include Compounds 15-20, 29, and 30 below:

Compound 15

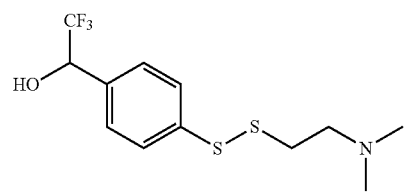

Compound 16

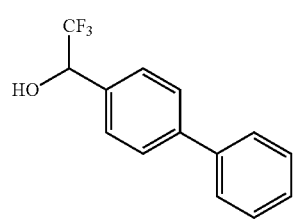

Compound 17

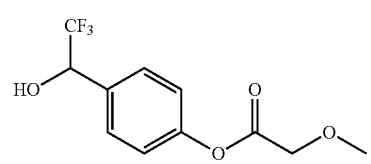

Compound 18

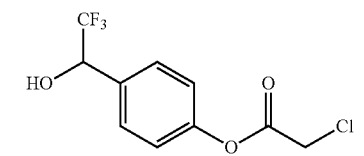

Compound 19

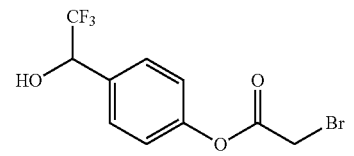

Compound 20

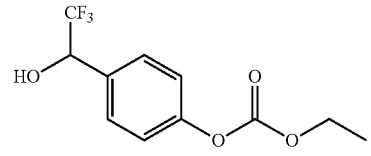

Compound 29

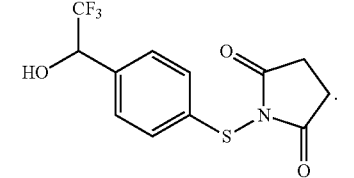

Compound 30

In some embodiments, when $R_7$ in formula (IV) is H, X can be N. In these compounds, $R_3$ can be S—S—$R_a$, $OR_a$, or $OC(O)R_a$, in which $R_a$ can be $C_1$-$C_{10}$ alkyl (e.g., $CH_3$) optionally substituted with halo, OR, OC(O)R$_a$, C$_3$-C$_{20}$ cycloalkyl, C$_1$-C$_{20}$ heterocycloalkyl, aryl, or heteroaryl, R being H or C$_1$-C$_{10}$ alkyl; and each of R$_2$, R$_4$, and R$_5$ can be H. An example of such an intermediate compound is Compound 21 below:

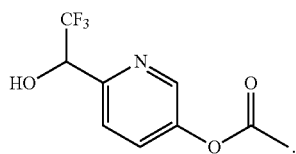

Compound 21

Referring to formula (IV), a subset of intermediate compounds includes those in which R$_7$ is OS(O)$_2$(CH$_2$)$_m$R$_d$, in which m can be 3 or 4; R$_d$ can be halo (e.g., Cl, Br, or I), tosylate, mesylate, or triflate. In these compounds, X can be C(R$_1$), in which R$_1$ can be H; R$_3$ can be C$_1$-C$_{10}$ alkyl (e.g., CH$_3$), and each of R$_2$, R$_4$, and R$_5$ can be H. Examples of such intermediate compounds include Compounds 22, 23, 31, and 32 below:

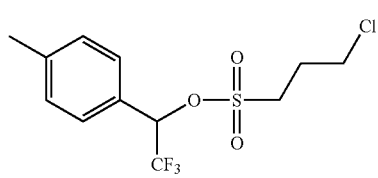

Compound 22

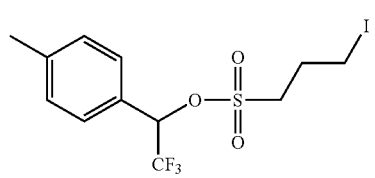

Compound 23

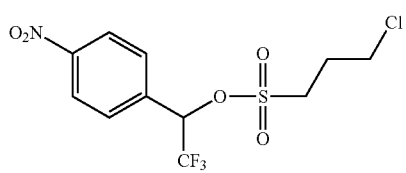

Compound 31

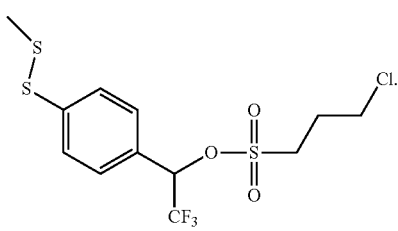

Compound 32

Referring to formula (IV), a subset of intermediate compounds includes those in which R$_7$ is Si(R$_e$R$_f$R$_g$), in which each of R$_e$, R$_f$, and R$_g$, independently, can be C$_1$-C$_{10}$ alkyl (e.g., CH$_3$). In these compounds, X can be C(R$_1$), in which R$_1$ can be H; R$_3$ can be S—R$_a$, in which R$_a$ can be C$_1$-C$_{10}$ alkyl (e.g., CH$_3$); and each of R$_2$, R$_4$, and R$_5$ can be H. An example of such an intermediate compound is Compound 33 below:

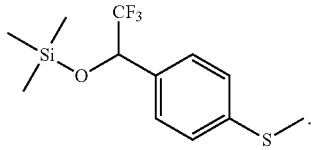

Compound 33

The intermediate compounds can be used to prepare the sulfonate compounds described herein by methods known in the art. For example, a sulfonate compound described herein can be prepared by (1) converting a compound containing a fluorophore covalently bonded with a sulfonic acid group to a sulfonyl chloride and (2) reacting the sulfonyl chloride with an intermediate compound of formula (IV) in which R$_7$ is H. As another example, a sulfonate compound described herein can be prepared by reacting a compound containing a fluorophore and a nucleophilic group with an intermediate compound of formula (IV) in which R$_7$ is OS(O)$_2$(CH$_2$)$_3$R$_d$.

Methods of Preparing Sulfonate Compounds and Intermediate Compounds

The sulfonate and intermediate compounds described herein can be prepared by methods well known in the art. Examples 1-21 below provide detailed descriptions of how Compounds 1, 2, 9-16, and 18-35 described above were actually prepared.

Scheme I shown below illustrates a typical synthetic route for synthesizing certain exemplary sulfonate compounds. Specifically, as shown in Scheme I, a sulfonate compound can be prepared by reacting a compound containing a fluorophore and a sulfonyl chloride group with an intermediate compound of formula (IV) in which R$_7$ is H.

Scheme I

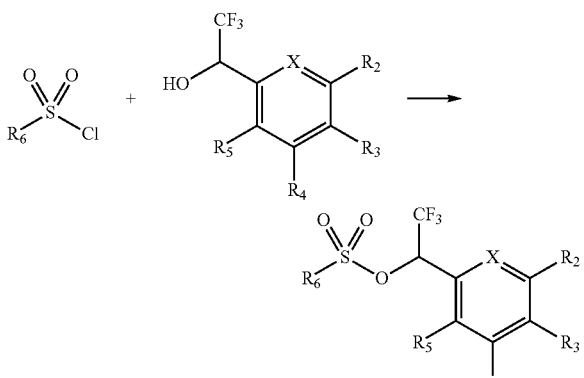

X and R$_2$-R$_6$ are defined above

Scheme II shown below illustrates another typical synthetic route for synthesizing certain exemplary sulfonate compounds. Specifically, as shown in Scheme II, a sulfonate compound can be prepared by reacting a compound containing a fluorophore and two nucleophilic groups with an intermediate compound of formula (IV) in which R$_7$ is OS(O)$_2$(CH$_2$)$_3$R$_d$.

Scheme II

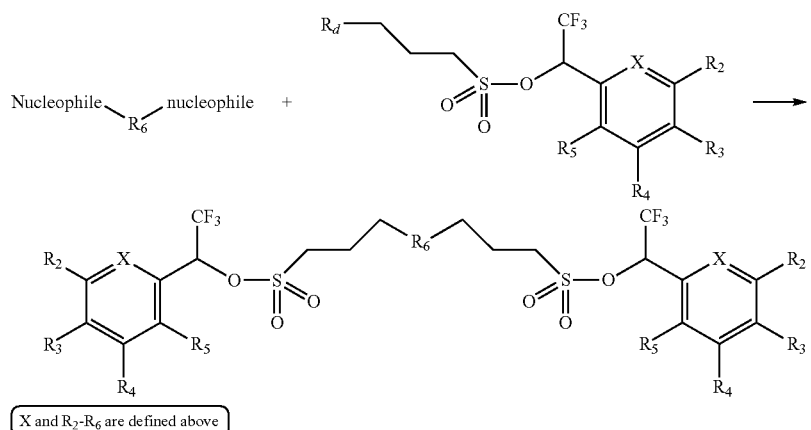

X and $R_2$-$R_6$ are defined above

Other sulfonate compounds can be prepared by using other suitable starting materials through the above synthetic routes and others known in the art. The methods described above may also include additional steps, either before or after the steps described specifically herein, to add or remove suitable protecting groups in order to ultimately allow synthesis of the sulfonate compounds. In addition, various synthetic steps may be performed in an alternate sequence or order to give the desired compounds. Synthetic chemistry transformations and protecting group methodologies (protection and deprotection) useful in synthesizing applicable sulfonate compounds are known in the art and include, for example, those described in R. Larock, *Comprehensive Organic Transformations*, VCH Publishers (1989); T. W. Greene and P. G. M. Wuts, *Protective Groups in Organic Synthesis*, 2nd Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Methods of Using Sulfonate Compounds

In general, the sulfonate compounds described herein can be used in an imaging method. The method can include (1) delivering one or more of the sulfonate compounds described above into a cell (e.g., by contact one or more of the sulfonate compounds with a cell); and (2) irradiating the cell with an excitation light, thereby generating fluorescence from the cell. In addition, the method can also include a step of detecting the fluorescence generated from the cell.

In some embodiments, the sulfonate compounds described herein can generate near-IR fluorescence light in a live cell. In some embodiments, the near-IR fluorescence light can have a wavelength of at least about 600 nm (e.g., at least about 650 nm, at least about 700 nm, or at least about 750 nm) and/or at most about 1000 nm (e.g., at most about 950 nm, at most about 900 nm, at most about 850 nm, or at most about 800 nm).

In some embodiments, the excitation light can have a wavelength in the same range as the fluorescence light generated by the sulfonate compounds described herein. For example, the sulfonate compounds can have a wavelength of at least about 600 nm (e.g., at least about 650 nm, at least about 700 nm, or at least about 750 nm) and/or at most about 1000 nm (e.g., at most about 950 nm, at most about 900 nm, at most about 850 nm, or at most about 800 nm).

In some embodiments, the sulfonate compounds described herein can be used as fluorescent sensors to identify proteins or metals or to detect enzymatic activity or efflux pump activity. For example, when a sulfonate compound contains a Tag, the sulfonate compound can be delivered to the cytoplasm of a cell where the Tag can be covalently bonded to a protein (e.g., an enzyme) to be detected. Upon irradiation of an excitation light, the sulfonate-protein conjugate can emit fluorescence, indicating the presence or activities of the protein in the cell. As another example, certain sulfonate compounds described herein can be pumped out of a cell by an efflux pump after they are delivered into a cell and deprotected. Thus, upon irradiation of an excitation light, the fluorescence emitted by a deprotected sulfonate compound can be used to detect the activity of the efflux pump. In addition, such a method can be used as a screen assay to identify drugs that can inhibit the activity of an efflux pump.

The methods described herein can be practiced with any suitable imaging system (e.g., an in vivo imaging system) that can detect fluorescence (e.g., near infrared fluorescence) by using a suitable detector (e.g., a sensitive CCD camera). Examples of such imaging systems have been described, e.g., in Doyle et al., *Cellular Microbiology* (2004) 6(4):303-317. Other suitable imaging systems are available from Perkin Elmer (e.g., Xenogen IVIS), Hamamatsu, Roper, and Kodak.

The contents of all publications cited herein (e.g., patents, patent application publications, and articles) are hereby incorporated by reference in their entirety.

The following examples are illustrative and not intended to be limiting.

Example 1

Preparation of Compound 1

2,2,2-trifluoro-1-(4-(methyldisulfanyl)phenyl)-ethyl 5-(dimethylamino)naphthalene-1-sulfonate

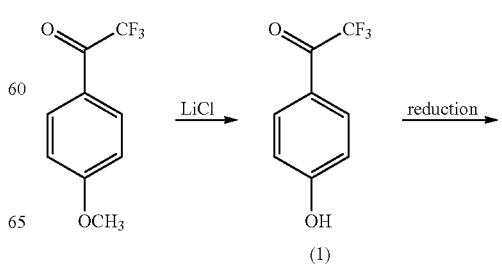

(1)

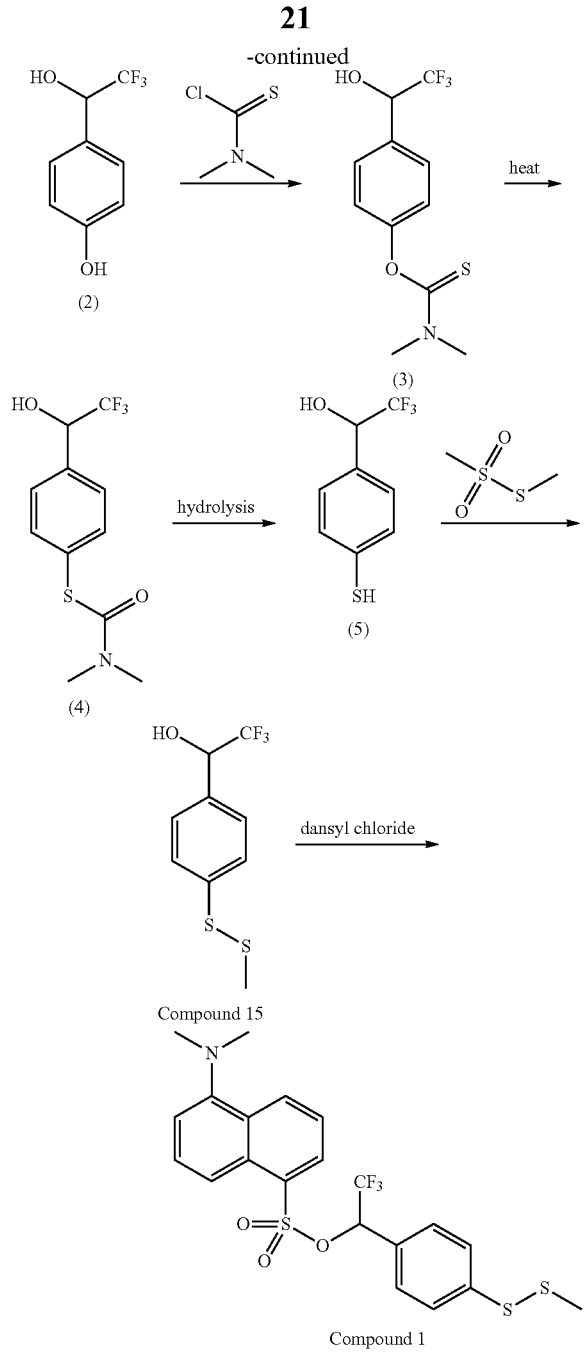

Compound 15

Compound 1

Synthesis of 2,2,2-Trifluoro-1-(4-hydroxy-phenyl)-ethanone (1)

2,2,2-Trifluoro-1-(4-methoxy-phenyl)-ethanone (5 g, 25 mmol) was added to a solution of lithium chloride (3 g, 71 mmol) in DMF (84 mL). After the reaction mixture was refluxed for 5 days, it was cooled to room temperature and then quenched with 200 mL 1M HCl. The mixture thus formed was extracted with diethyl ether (3×100 mL). The combined organic phases were washed with $H_2O$ (3×300 mL), followed by brine (1×200 mL) and then dried over $Na_2SO_4$. The organic phase was collected by filtration and concentrated by rotary evaporation to yield yellow oil. The crude material was purified by flash column chromatography (0-25% ethyl acetate/hexanes) to yield intermediate compound (1) as a beige solid (4.1 g, 88%). $^1H$ NMR (400 MHz, DMSO-$D_6$): δ 11.14 (s, 1H), 7.94 (m, 2H), 6.98 (m, 2H); $^{19}F$ NMR (376 MHz, $CDCl_3$): δ −70.4.

Synthesis of 4-(2,2,2-Trifluoro-1-hydroxy-ethyl)-phenol (2)

2,2,2-Trifluoro-1-(4-hydroxy-phenyl)-ethanone (1) (4.1 g, 21.6 mmol) was dissolved in MeOH (50 mL) at 0° C. $NaBH_4$ (1.6 g, 42.2 mmol) was slowly added to the above solution. After 20 minutes, the reaction mixture was quenched with 300 ml of 1M HCl. The mixture thus formed was extracted with ethyl acetate (3×100 mL). The combined organic phases were washed with $H_2O$ (3×100 mL), followed by brine (1×200 mL) and then dried over $Na_2SO_4$. The organic phase was collected by filtration and concentrated by rotary evaporation to yield a white solid. Recrystallization of the solid with $CHCl_3$ yields intermediate compound (2) as fluffy white crystals (3.14 g, 76%). $^1H$-NMR (CD3OD): δ 7.28 (d, 2H, J=8.7 Hz), 6.78 (m, 2H), 4.89 (q, 1H, J=7.2 Hz); $^{19}F$ NMR (CD3OD): δ −80.4 (d, J=7.2 Hz); $^{13}C$-NMR (CD3OD): δ 158.0, 128.9, 126.4, 125.2 (q, $J_{CF}$=280 Hz), 114.9, 71.7 (q, $J_{CF}$=31 Hz).

Synthesis of Dimethyl-thiocarbamic acid O-[4-(2,2,2-trifluoro-1-hydroxy-ethyl)-phenyl]ester (3)

4-(2,2,2-Trifluoro-1-hydroxy-ethyl)-phenol (2) (350 mg, 1.8 mmol) and DABCO (217 mg, 1.9 mmol) were dissolved in NMP (1 mL) and heated to 50° C. To this solution, dimethylthiocarbamoyl chloride (248 mg, 2 mmol) dissolved in NMP (0.5 mL) was added dropwise. After 4 hours, the reaction temperature was lowered to room temperature. The reaction mixture was then poured into $H_2O$ (20 mL). The crude material was extracted with ethyl acetate (3×30 mL). The combined organic phases were washed with $H_2O$ (3×50 mL), then brine (1×30 mL), and finally dried over $Na_2SO_4$. The organic phase was collected by filtration and concentrated by rotary evaporation to yield a yellow oil. Flash column chromatography of the oil on silica gel with 0-15% ethyl acetate/hexanes yielded intermediate compound (3) as a sticky yellow solid (342 mg, 67%). $^1H$ NMR (400 MHz, $CDCl_3$): δ 7.52 (d, 2H, J=8.4 Hz) 7.13 (d, 2H, J=8.65 Hz), 5.06 (q, 1H, J=6.57 Hz), 3.46 (s, 3H), 3.35 (s, 3H); $^{19}F$ NMR (376 MHz, $CDCl_3$): δ −78.8 (d, 6.64 Hz). ES-HRMS calc'd for $C_{11}H_{13}F_3NO_2S$: 280.0619. found 280.0582.

Synthesis of Dimethyl-thiocarbamic acid S-[4-(2,2,2-trifluoro-1-hydroxy-ethyl)-phenyl]ester (4)

In a crimp-sealed 10 mL CEM microwave synthesis tube, dimethyl-thiocarbamic acid O-[4-(2,2,2-trifluoro-1-hydroxy-ethyl)-phenyl]ester (3) (240 mg, 0.86 mmol) was dissolved in NMP (1 mL). The tube was placed into a CEM microwave synthesizer with the following settings: max temp: 220° C., ramp time: 5 minutes, hold time: 25 minutes, max power: 300 W, and max pressure: 100 psi. After the reaction was completed and the temperature cooled to room temperature, the crude material was extracted with ethyl acetate (3×30 mL). The combined organic phases were washed with $H_2O$ (3×30 mL), followed by brine (1×30 mL) and then dried over $Na_2SO_4$. The organic phase was collected by filtration and concentrated by rotary evaporation to yield yellow oil. Flash column chromatography of the oil on silica gel with 0-30% ethyl acetate/hexanes yielded intermediate compound (4) as a pale yellow solid (164 mg, 68%). $^1H$ NMR (400 MHz, $CD_3OD$): δ 7.52 (m, 4H), 5.07 (q, J=7.04, 1H), 3.09 (s, 3H), 2.98 (s, 3H); $^{19}$F NMR (376 MHz, CD$_3$OD): δ −79.9 (d, J=7.1 Hz); $^{13}$C NMR (100 MHz, CD$_3$OD): δ 167.4, 137.1, 135.4, 129.6, 128.1, 125 (q, J$_{CF}$=281.8 Hz), 71.4 (q, J$_{CF}$=31.4 Hz), 36.1. ES-HRMS calc'd for C$_{11}$H$_{13}$F$_3$NO$_2$S: 280.0619. found 280.0603.

Synthesis of
2,2,2-Trifluoro-1-(4-mercapto-phenyl)-ethanol (5)

In a 2-neck round bottom flask, NaOH (330 mg, 5.5 mmol) and dimethyl-thiocarbamic acid S-[4-(2,2,2-trifluoro-1-hydroxy-ethyl)-phenyl]ester (4) (16 mg, 0.59 mmol) was dissolved in THF (5 mL) and MeOH (0.82 mL) under argon at 69° C. After 3 hours, the reaction mixture was quenched under argon with 1M HCl (3 mL) and was extracted with ethyl acetate (3×30 mL). The combined organic phases were washed with H$_2$O (3×30 mL), followed by brine (1×30 mL), and then dried over Na$_2$SO$_4$. The organic phase was collected by filtration and concentrated by rotary evaporation to yield intermediate compound (5) as a yellow oil (107 mg, 65%). $^1$H NMR (400 MHz, CHCl$_3$): δ 7.53 (m, 2H), 7.43 (d, J=8.68, 2H), 5.01 (q, J=6.55, 1H); $^{19}$F NMR (376 MHz, CDCl$_3$): −79 (d, J=6.7 Hz); $^{13}$C NMR (100 MHz, CDCl$_3$): δ 133.2, 131.5, 129.3, 128.4, 124.4 (q, J$_{CF}$=282.1 Hz), 72.5 (q, J$_{CF}$=32 Hz).

Synthesis of
Trifluoro-1-(4-methyldisulfanyl-phenyl)-ethanol
(Compound 15)

Methanethiosulfonic acid S-methyl ester (0.02 ml, 0.22 mmol) was dissolved in an EtOH (0.46 mL) and saturated NaCO$_3$/H$_2$O (pH 8) solution (0.8 mL) under argon at 0° C. A solution of 2,2,2-trifluoro-1-(4-mercapto-phenyl)-ethanol (5) (22 mg, 0.11 mmol) dissolved in THF (1.5 mL) under argon was added dropwise. After 10 minutes, the reaction temperature was raised to room temperature. After 36 hours, the reaction was extracted with ethyl acetate (3×30 mL) and H$_2$O (30 mL). The combined organic phases were dried over Na$_2$SO$_4$ and under reduced pressure. Flash chromatography on silica gel using 0-30% acetone/hexane gave Compound 15 as a yellow oil (23 mg, 86% yield). $^1$H NMR (400 MHz, CDCl$_3$): δ 7.5 (m, 4H), 5.02 (q, J=6.7 Hz, 1H), 2.45 (s, 3H); $^{19}$F NMR (376 Hz, CDCl$_3$) δ −78.79 (d); $^{13}$C NMR (100 MHz, CH3OD): δ 137.6, 134.2, 128.8, 126.4, 124.6 (q, J$_{CF}$=281.7 Hz), 71 (q, J$_{CF}$=31.5 Hz), 21.5.

Synthesis of 5-Dimethylamino-naphthalene-1-sulfonic acid 2,2,2-trifluoro-1-(4-methyldisulfanyl-phenyl)-ethyl ester (Compound 1)

2,2,2-Trifluoro-1-(4-methyldisulfanyl-phenyl)-ethanol (6) (12 mg, 0.047 mmol) and dansyl chloride (15 mg, 0.057 mmol) were dissolved in dry CH$_2$Cl$_2$ (0.2 mL). A solution of DABCO (63 mg, 0.56 mmol) dissolved in dry CH$_2$Cl$_2$ (0.1 mL) was added dropwise to the above solution. After 4 hours at room temperature, the reaction was poured into H$_2$O (30 mL) and extracted with ethyl acetate (3×30 mL). The combined organic phases were washed with H$_2$O (3×30 mL), followed by brine (1×30 mL) and then dried over Na$_2$SO$_4$. The organic phase was collected by filtration and concentrated by rotary evaporation. Flash chromatography on silica gel using 0-15% acetone/hexanes to yield Compound 1 as a yellow solid (6.5 mg, 28%). $^1$H NMR (400 MHz, CDCl$_3$): δ 8.46 (d, J=8.5 Hz, 1H), 8.2 (d, J=8.7 Hz, 1H), 8.07 (d, J=7.3 Hz, 1H), 7.57 (t, J=7.9 Hz, 1H), 7.37 (t, J=8.2 Hz, 1H), 7.16 (d, J=7.2 Hz, 1H), 7.13 (d, J=8.4 Hz, 2H), 7.03 (d, J=8.3 Hz, 2H), 5.59 (q, J=6.3 Hz, 1H), 2.84 (s, 6H), 2.37 (s, 3H); $^{19}$F NMR (376 MHz, CDCl$_3$): δ −76.3 (d, J=6.3 Hz). HRMS calc'd for C$_{21}$H$_{21}$F$_3$NO$_3$S$_3$: 488.0636. found: 488.0647.

Example 2

Preparation of Compound 2

1-(4-(2-(dimethylamino)ethyl)disulfanyl)-phenyl)-2,2,2-trifluoroethyl 5-(dimethylamino)naphthalene-1-sulfonate

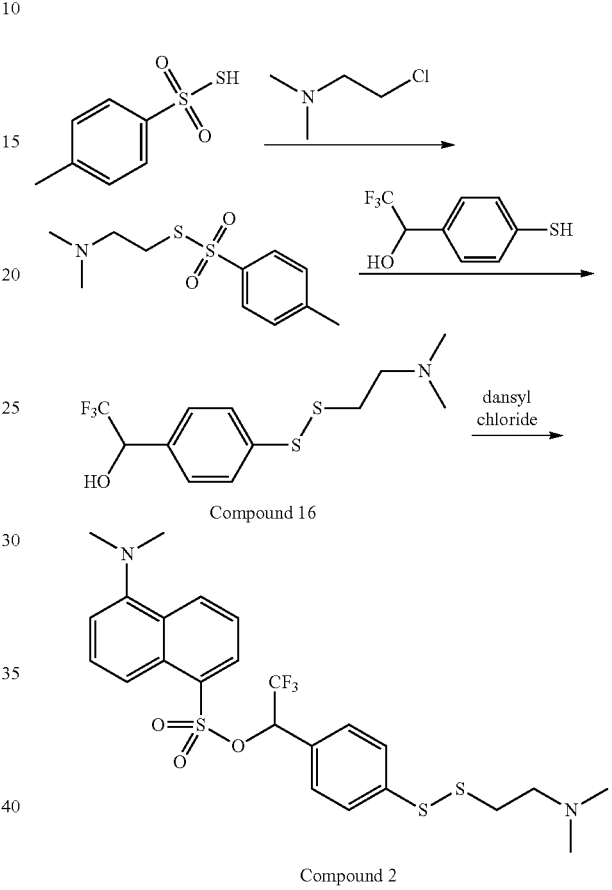

Compound 16

Compound 2

Toluene-4-thiosulfonic acid
S-(2-dimethylamino-ethyl) ester

Toluene-4-s thiosulfonate (200 mg, 0.88 mmol) and (2-chloro-ethyl)-dimethyl-amine (177 mg, 1.32 mmol) were dissolved in methanol (5 mL). After the reaction mixture was refluxed for 21 hours, it was poured into H$_2$O (30 mL). The mixture thus formed was extracted using ethyl acetate (3×30 mL). The combined organic phases were washed with H$_2$O (3×30 mL), followed by brine (1×30 mL) and then dried over Na$_2$SO$_4$ to yield crude toluene-4-thiosulfonic acid S-(2-dimethylamino-ethyl) ester as a white oil (30 mg, 13% yield), which was used using in the next synthetic step without further purification.

1-[4-(2-Dimethylamino-ethyldisulfanyl)-phenyl]-2,2,2-trifluoro-ethanol (Compound 16)

Crude toluene-4-thiosulfonic acid S-(2-dimethylaminoethyl) ester obtained above (30 mg) was dissolved in a solution containing EtOH (0.8 mL) and saturated aqueous NaHCO$_3$ (1.5 mL) under argon at 0° C. A solution of 2,2,2- trifluoro-1-(4-mercapto-phenyl)-ethanol obtained in Example 1 (50 mg, 0.24 mmol) dissolved in THF (1.9 mL) was added dropwise to the above solution under argon. After 10 minutes, the reaction temperature was raised to room temperature. After 3 hours, the reaction mixture was poured into H₂O (30 mL) and extracted with ethyl acetate (3×30 mL). The combined organic phases were washed with H₂O (3×30 mL), followed by brine (1×30 mL) and then dried over Na₂SO₄. The organic phase was collected by filtration and concentrated by rotary evaporation to yield crude Compound 16 as yellow oil (30 mg), which was used in the next synthetic step without further purification.

5-Dimethylamino-naphthalene-1-sulfonic acid 1-[4-(2-dimethylamino-ethyldisulfanyl)-phenyl]-ethyl ester (Compound 2)

Dansyl chloride (37.5 mg, 0.13 mmol) dissolved in dry CH₂Cl₂ (0.5 mL) was added to the crude 1-[4-(2-dimethylamino-ethyldisulfanyl)-phenyl]-2,2,2-trifluoro-ethanol obtained above. To this solution was added dropwise a solution of DABCO (157 mg, 1.4 mmol) dissolved in dry CH₂Cl₂ (0.25 mL). After 4 hours at room temperature, the reaction mixture was poured into H₂O (30 mL) and extracted using ethyl acetate (3×30 mL). The combined organic phases were washed with H₂O (3×30 mL), followed by brine (1×30 mL) and then dried over Na₂SO₄. The organic phase was collected by filtration and concentrated by rotary evaporation. The crude product thus formed was purified by using flash chromatography on silica gel using 0-2% CH₂Cl₂/MeOH to yield Compound 2 a yellow oil (8 mg). ¹H NMR (400 MHz, CD₃OD): δ 8.45 (m, 1H), 8.13 (m, 2H), 7.57 (m, 1H), 7.43 (m, 1H), 7.27 (m, 1H), 7.06 (m, 2H), 6.98 (d, J=8.47, 2H), 5.88 (q, J=6.5 Hz, 1H), 2.8 (s, 6H), 2.78 (m, 2H), 2.57 (m, 2H), 2.21 (s, 6H); ¹⁹F NMR (376 MHz, CH₃OD): δ −78.1 (d, J=6.5 Hz).

Example 3

Preparation of Compound 9

6-(1-(((5-(dimethylamino)naphthalen-1-yl)sulfonyl)oxy)-2,2,2-trifluoroethyl)pyridin-3-yl 2-methoxyacetate

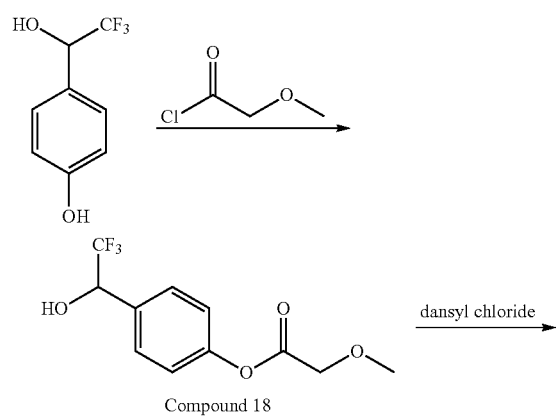

Compound 18

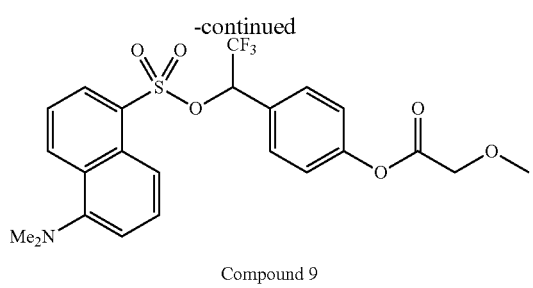

Compound 9

Compound 18

To a 4 mL vial equipped with a magnetic stir bar were added 4-(2,2,2-trifluoro-1-hydroxy-ethyl)-phenol obtained in Example 1 (150 mg, 0.8 mmol), anhydrous THF (1.5 mL) and triethylamine (90 mg, 0.88 mmol). The reaction mixture was stirred on ice bath for 10 minutes. Methoxyacetyl chloride (95 mg, 0.88 mmol) dissolved in 0.5 mL of THF was added to the reaction mixture dropwise. The reaction mixture was then removed from the ice bath and stirred for 1 hour at room temperature. After THF was removed by vacuumed, the crude product thus formed was purified by flash chromatography over silica gel in 1-5% methanol/dichloromethane. An amber liquid was collected which turned into a white solid under high vacuum overnight (Compound 18; 190 mg; 90% yield).

Compound 9

To a 25 mL flask were added dansyl chloride (100 mg, 0.37 mmol), anhydrous dichloromethane (3 mL), and Compound 18 obtained above (MeOAcOTFMB, 117 mg, 0.44 mmol). After cooling on ice for 5 minutes, DABCO (50 mg, 0.44 mmol) dissolved in 0.5 mL of dichloromethane was added dropwise. The reaction mixture was removed from the ice bath and stirred at room temperature for two hours. The crude product thus formed was purified by flash column chromatography on silica gel with 5-50% ethyl acetate/hexanes to give Compound 9 (MeOAcOTFMB-Dan) as a yellow oil (31 mg, 17% yield).

Example 4

Preparation of Compound 10

6-(1-(((5-(dimethylamino)naphthalen-1-yl)sulfonyl)oxy)-2,2,2-trifluoroethyl)pyridin-3-yl 2-chloroacetate

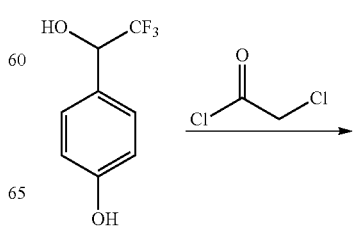

27
-continued

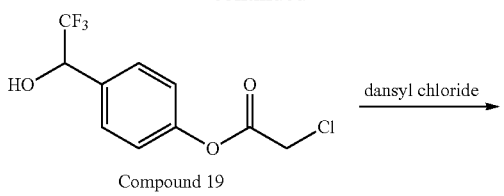

Compound 19

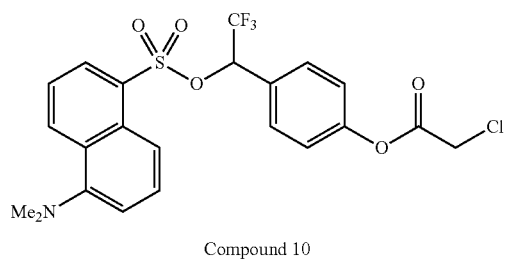

Compound 10

Compound 19

To a round bottom flask containing 4-(2,2,2-trifluoro-1-hydroxy-ethyl)-phenol obtained in Example 1 (200 mg, 1.04 mmol) and 3 mL of THF was added triethyl amine (111 mg, 1.1 mmol). After the reaction mixture was put on ice, chloroacetyl chloride (124 mg, 1.1 mmol) dissolved in 1 ml of THF was added dropwise. After a precipitate formed, the THF was removed by vacuum. The crude product thus formed was purified by flash column chromatography on silica gel using 0-20% ethyl acetate/hexanes as the eluent to give Compound 19 as a white solid (205 mg, 73% yield).

Compound 10

Dansyl chloride (0.37 mmol, 100 mg) in dichloromethane (1 ml) was stirred at 0° C. Compound 19 obtained above was added (110 mg, 0.407 mmol) to the above solution. After cooling on ice, DABCO dissolved in 0.5 mL of dichloromethane was added dropwise. The reaction mixture was removed from the ice bath and stirred at room temperature for 1 hour. The crude product thus formed was purified by flash column chromatography using 0-30% ethyl acetate/hexanes.

Example 5

Preparation of Compound 11

6-(1-(((5-(dimethylamino)naphthalen-1-yl)sulfonyl)oxy)-2,2,2-trifluoroethyl)pyridin-3-yl 2-morpholinoacetate To a 4 ml vial were added compound 19 obtained in Example 6 above (200 mg, 0.25 mmol), 5 mL of acetone, and morpholine (143 mg, 1.64 mmol). The reaction was stirred overnight at room temperature. After the salt thus formed was removed by filtration, the remaining reaction mixture was purified by flash column chromatography on silica gel with ethyl acetate/hexanes to yield Compound 11 as yellow oil (62 mg, 26% yield).

28

Example 6

Preparation of Compound 12

6-(1-(((5-(dimethylamino)naphthalen-1-yl)sulfonyl)oxy)-2,2,2-trifluoroethyl)pyridin-3-yl acetate

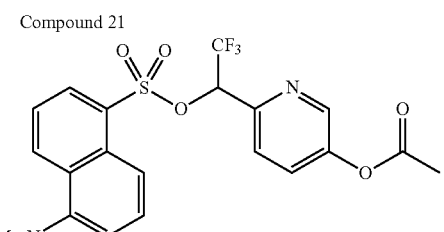

Compound 21

[Compound 12 structure]

Compound 12

Compound 21

3-Hydroxy-6-(1-hydroxy-2,2,2-trifluoroethyl)pyridine (0.79 mmol, 152 mg) (which was prepared as described in *J. Het. Chem.*, 38 p25 (2001)) was dissolved in THF (2 ml). Triethylamine (0.11 ml, 0.79 mmol) and acetyl chloride (56.6 µl, 0.79 mmol) were added to the above solution. After the mixture thus formed was stirred for 2 hours at room temperature, the volatiles were removed under vacuum and the crude material was redissolved in dichloromethane and purified by flash chromatography (0-25% EtOAc/hexanes) to give Compound 21. $^1$H-NMR (CDCl$_3$): δ 8.43 (d, 1H, J=2.8 Hz), 7.59 (dd, 1H, J=2.8 Hz, 8.8 Hz), 7.46 (d, 1H, J=8.8 Hz), 5.22 (d, 1H, J=6.8 Hz), 5.03 (m, 1H), 2.34 (s, 3H). $^{19}$F-NMR: δ −78.48 (d, J=6.8 Hz). $^{13}$C-NMR: δ 168.9, 148.4, 148.1, 142.2, 130.8, 124.1 (q, J=281 Hz), 123.2, 70.9 (q, J=31.5), 21.2.

Compound 12

DABCO (13.4 mg, 0.12 mmol) was added to a solution containing Compound 21 obtained above (23.4 mg, 0.1 mmol) and dansyl chloride (27 mg, 0.1 mmol) in 0.5 ml dichloromethane. After the reaction was complete, the product was isolated by flash chromatography (0-25% EtOAc/hexanes) to give Compound 12 (25 mg) as a yellow oil. $^1$H-NMR (CDCl$_3$): δ 8.51 (dt, 1H, J=1.2, 8.4 Hz), 8.23 (d, 1H, J=8.4 Hz), 8.18 (dd, 1H, J=1.6 Hz, 7.6 Hz), 8.16 (d, 1H, J=2 Hz), 7.57 (dd, 1H, J=8.4 Hz, 7.6 Hz), 7.45 (dd, 1H, J=8.4 Hz, 7.6 Hz), 7.32 (d, 1H, J=8.4 Hz), 7.19 (dd, 1H, J=3.2, 8.8 Hz), 7.17 (d, 1H, J=8.4 Hz), 5.75 (q, J=6 Hz), 2.85 (s, 6H), 2.29 (s, 3H). $^{19}$F-NMR: δ −75.78 (d, J=5.8 Hz).

Example 7

Preparation of Compound 13

1,11-bis-[3-(2,2,2-trifluoro-1-p-tolyl-ethoxysulfonyl)-propyl]-3,4,8,9,10,11-hexahydro-2H-13-oxa-6,11-diaza-1-azonia-pentacene tetrafluoroborate Compound 13 was prepared by using the method described in Pauff et al., *J. Org. Chem.*, 2013, 78, 711-716. Mp 220-222° C. (dec.); $^1$H-NMR (400 MHz, CD$_3$OD): δ 7.47 (s, 2H), 7.43 (d, 4H, J=8.1 Hz), 7.21 (d, 4H, J=8 Hz), 6.81 (s, 2H), 6.07 (q, 2H, J$_{HF}$=6.5 Hz), 3.74-3.61 (m, 4H), 3.55 (t, 4H, J=5.5 Hz), 3.45-3.33 (m, 4H), 2.90 (t, 4H, J=6 Hz), 2.28 (s, 6H), 2.15-2.07 (m, 4H), 1.99 (p, 4H, J=5.5 Hz). $^{19}$F-NMR (376 MHz, CD$_3$OD): δ −78.0 (d, J=6.5 Hz), −154.58 (s), −154.6 (s) (BF$_4^-$ counterion). $^{13}$C-NMR (100 MHz, CD$_3$OD): δ 154.6, 148.7, 141.1, 134.4, 130.8, 129.5, 129.4, 128.2, 127.4, 122.9 (q, $^1$J$_{CF}$=280 Hz), 95.0, 77.7 (q, $^2$J$_{CF}$=34 Hz), 50.64, 50.6, 27.2, 20.6, 20.5, 20.1. HRMS (EI) m/z: [M]+ Calcd for C$_{42}$H$_{44}$F$_6$N$_3$O$_7$S$_2$: 880.2525. found: 880.2511.

Example 8

Preparation of Compound 14

1-ethyl-2-((1E,3E,5E)-5-(1-ethyl-3,3-dimethyl-5-((2,2,2-trifluoro-1-(4-(2-methoxyacetoxy)phenyl)ethoxy)sulfonyl)indolin-2-ylidene)penta-1,3-dien-1-yl)-3,3-dimethyl-5-((2,2,2-trifluoro-1-(4-(2-methoxyacetoxy)-phenyl)ethoxy)sulfonyl)-3H-indol-1-ium

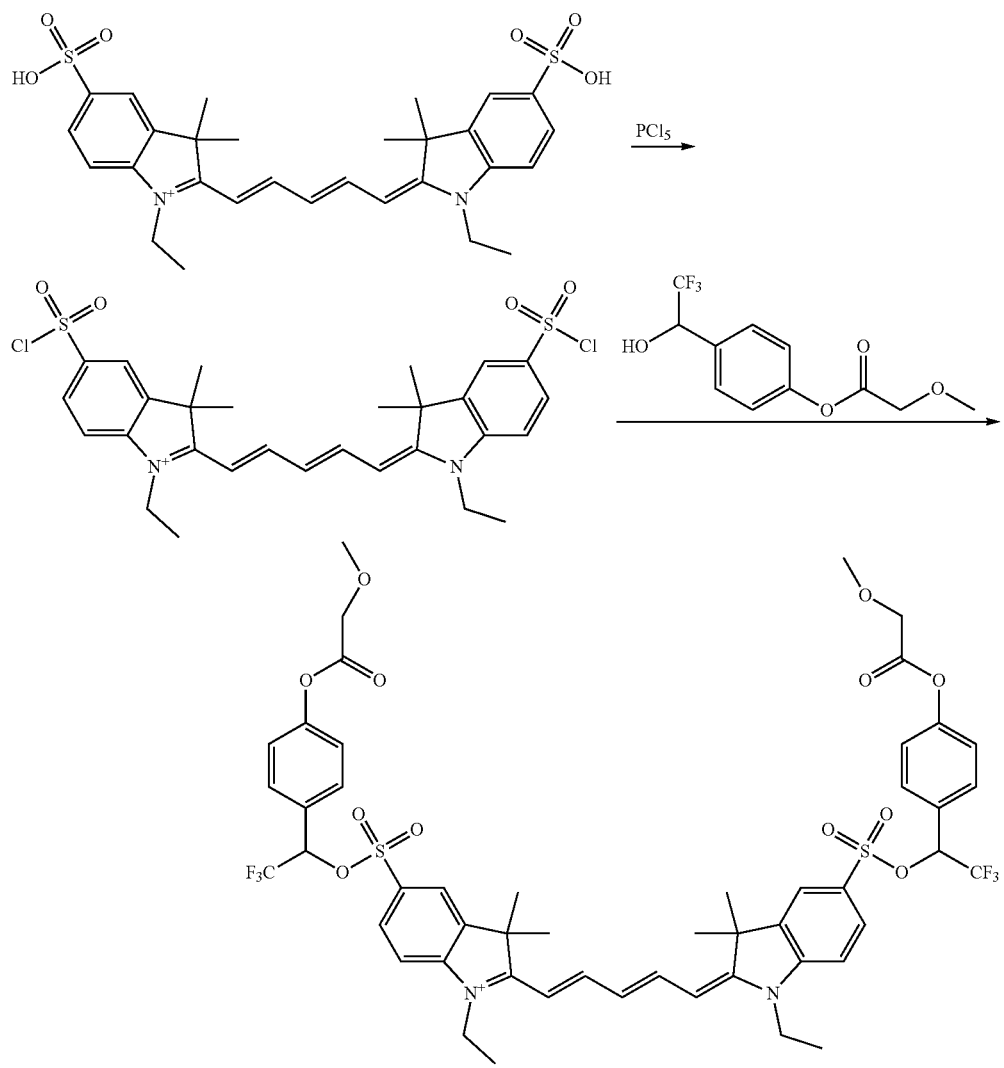

Compound 14

To a dry 5 mL round bottom flask was added a magnetic stir bar. The flask was capped and put under argon. After Cy5 (SO$_3$)$_2$ (50 mg, 0.088 mmol, 1 eq) was added to the flask, PCl$_5$ (64 mg, 0.308 mmol, 3.5 eq) was added. POCl$_3$ (0.7 mL, 7.60 mmol) was then added and served as the solvent to the reaction. The reaction mixture was heated to 60° C. for 50 minutes, cooled down to room temperature for ten minutes, then poured on ice water, at which point the crude product crashed out. The crude product was extracted with dichloromethane from the ice water, washed twice with ice water (50 mL), once with brine (50 mL), and dried with Na$_2$SO$_4$. The organic layer was concentrated in vacuo and the Cy5(SO$_2$Cl)$_2$ was used in the next step without further purification.

Cy5(SO$_2$Cl)$_2$ (54 mg, 0.088 mmol, 1.0 eq) obtained above was added to a 5 mL round bottom flask under argon, followed by Compound 17 (MeOAcOTFMB, 58 mg, 0.22 mmol, 2.5 eq) obtained in Example 5 below dissolved in dichloromethane (1.5 mL). After the flask was put on ice bath, DABCO (25 mg, 0.22 mmol, 2.5 eq) dissolved in 0.5 mL of dichloromethane was added to the reaction mixture dropwise. After the addition of DABCO, the flask was removed from the ice bath and stirred at room temperature for 2 hours. In 10% methanol/dichloromethane, the Rf of the product dye was 0.65. A silica gel column was used to purify the product using 0% to 5% methanol/dichloromethane, followed by HPLC purification from 0 to 100% acetonitrile/0.1% TFA in 100 minutes to isolate Compound 14 (Bis-MeOAcOTFMB-Cy5, 7.5 mg, 8% yield). $^1$H-NMR (CD$_3$OD): δ 8.35 (t, 2H, J=12.8 Hz), 7.85 (d, 2H, J=2 Hz), 7.80 (dd, 2H, J=2, 8.4 Hz), 7.35 (d, 4H, J=8.6 Hz), 7.27 (d, 2H, J=8.5 Hz), 6.98 (d, 4H, J=8.8 Hz), 6.76 (t, 1H, J=12.4 Hz), 6.41 (d, 2H, J=13.7 Hz), 6.11 (q, 2H, J$_{HF}$=6.4 Hz), 4.26 (s, 4H), 4.11 (q, 4H, J=7.3 Hz), 3.44 (s, 6H), 1.66 (s, 6H), 1.65 (s, 6H), 1.33 (t, 6H, J=7.2 Hz). $^{19}$F-NMR (CD$_3$OD): δ −78.45 (d, J=6.4 Hz), −77.4 (s, TFA salt).

Example 9

Preparation of Compound 20

4-(2,2,2-trifluoro-1-hydroxyethyl)phenyl 2-bromoacetate

Compound 20 was prepared in a manner similar to that used to prepare Compound 19 described in Example 4 except that chloroacetyl chloride was replaced with bromoacetyl chloride. Compound 20 was obtained as a white solid with a yield of 36%.

Example 10

Preparation of Compound 22

2,2,2-trifluoro-1-(p-tolyl)ethyl 3-chloropropane-1-sulfonate

Compound 22 was prepared by using the method described in Pauff et al., *J. Org. Chem.*, 2013, 78, 711-716. Mp 61-63° C.; $^1$H-NMR (400 MHz, CDCl$_3$): δ 7.38 (d, 2H, J=8.0 Hz), 7.26 (d, 2H, J=7.8 Hz), 5.74 (q, 1H, J$_{HF}$=6.4 Hz), 3.63-3.54 (m, 2H), 3.27-3.14 (m, 2H), 2.39 (s, 3H), 2.31-2.21 (m, 2H). $^{19}$F-NMR (376 MHz, CDCl$_3$): δ −76.3 (d, J=6.4 Hz). $^{13}$C-NMR (100 MHz, CDCl$_3$): δ 141.4, 130.0, 128.3, 126.8, 122.5 (q, $^1$J$_{CF}$=281 Hz), 78.3 (q, $^2$J$_{CF}$=35 Hz), 49.8, 42.3, 26.7, 21.6. HRMS (EI) m/z: [M+Na]+ Calcd for C$_{12}$H$_{14}$ClF$_3$O$_3$SNa: 353.0202. found: 353.0190.

Example 11

Preparation of Compound 23

2,2,2-trifluoro-1-(p-tolyl)ethyl 3-iodopropane-1-sulfonate

Compound 23 was prepared by using the method described in Pauff et al., *J. Org. Chem.*, 2013, 78, 711-716. $^1$H-NMR (400 MHz, CDCl$_3$): δ 7.39 (d, 2H, J=8.1 Hz), 7.27 (d, 2H, J=7.9 Hz), 5.73 (q, 1H, J$_{HF}$=6.4 Hz), 3.22-3.07 (m, 4H), 2.39 (s, 3H), 2.33-2.21 (m, 2H). $^{19}$F-NMR (376 MHz, CDCl$_3$): δ −76.3 (d, J=6.4 Hz). $^{13}$C-NMR (100 MHz, CD$_3$OD): δ 141.5, 130.1, 128.4, 126.8, 122.5 (q, $^1$J$_{CF}$=281 Hz), 78.3 (q, $^2$J$_{CF}$=34 Hz), 53.2, 27.2, 21.6, 2.1. HRMS (EI) m/z: [M+Na]+ Calcd for C$_{12}$H$_{14}$F$_3$IO$_3$SNa: 444.9558. found: 444.9520.

Example 12

Preparation of Compound 24

2-[7-(1,1-Dimethyl-3-{4-[2,2,2-trifluoro-1-(4-nitro-phenyl)-ethoxysulfonyl]-butyl}-1,3-dihydro-benzo[e]indol-2-ylidene)-hepta-1,3,5-trienyl]-1,1-dimethyl-3-{4-[2,2,2-trifluoro-1-(4-nitro-phenyl)-ethoxysulfonyl]-butyl}-1H-benzo[e]indolium chloride Indocyanine green (sodium 4-[2-[(1E,3E,5E,7E)-7-[1,1-dimethyl-3-(4-sulfonatobutyl)benzo[e]indol-2-ylidene]hepta-1,3,5-trienyl]-1,1-dimethylbenzo[e]indol-3-ium-3-yl]butane-1-sulfonate, 63 mg) was suspended in 1,2-dichloroethane (0.8 mL). After POCl$_3$ (70 μL, 0.75 mmol) was added to the mixture, the reaction mixture was heated to 65° C. and stirred for 5 hours. The reaction was then cooled to room temperature and ESi-MS was used to confirm production of the bis-sulfonyl chloride. ESI-MS calculated for C$_{43}$H$_{47}$Cl$_2$N$_2$O$_4$S$_2$$^+$: 789.23, observed: 789.3. The above reaction mixture was then cooled to 0° C. and used without work-up to prepare Compound 24.

2,2,2-Trifluoro-1-(4-nitro-phenyl)-ethanol (70 mg, 0.32 mmol) was dissolved in anhydrous dichloromethane (4 mL) and cooled to 0° C. in an ice bath. Triethylamine (0.3 mL, 2.2 mmol) was then added to the alcohol solution. The bis-sulfonyl chloride reaction mixture obtained above was added dropwise over 20 minutes to the alcohol solution. After the reaction mixture was stirred at 0° C. for 1 hour, it was diluted into 1 M HCl (100 mL) and extracted with ethyl acetate (120 mL). The organic phase was washed with 0.1 M HCl (3×50 mL), water (2×50 mL), and brine (2×75 mL) and dried over sodium sulfate. Evaporation of the solvent under vacuum resulted in the crude product as a green solid. The crude product was purified by flash column chromatography (0-7% methanol/dichloromethane) to yield Compound 24 as a green solid (6.2 mg, 6.4%). $^1$H-NMR (CD$_3$OD): δ 8.27 (d, 4H, J=8.8 Hz), 8.22 (dd, 2H, J=1.0 Hz, 8.6 Hz), 8.08-7.98 (m, 6H), 7.78 (d, 4H, J=8.8 Hz), 7.64 (ddd, 3H, J=1.3 Hz, 6.9 Hz, 8.4 Hz), 7.56 (d, 2H, J=8.9 Hz), 7.49 (ddd, 2H, J=1.1 Hz, 6.9 Hz, 8.1 Hz), 6.56 (t, 2H, J=12.6 Hz), 6.39-6.33 (m, 4H), 4.25 (d, 4H, J=6.5 Hz), 3.51-3.47 (m, 4H), 2.04-1.97 (m, 20H). $^{19}$F-NMR (CD$_3$OD): δ −77.8 (d, J=6.3 Hz). HR-EIMS m/z calculated for C$_{59}$H$_{57}$F$_6$N$_4$O$_{10}$S$_2$: 1159.3420. found: 1159.3414.

Example 13

Preparation of Compound 25

1,11-Bis-{3-[2,2,2-trifluoro-1-(4-nitro-phenyl)-ethoxysulfonyl]-propyl}-3,4,8,9,10,11-hexahydro-2H-13-oxa-6,11-diaza-1-azonia-pentacene chloride Sodium 1,11-bis-(3-sulfonatopropyl)-3,4,8,9,10,11-hexahydro-2H-13-oxa-6,11-diaza-1-azonia-pentacene (8 mg, 14 μmol) was suspended in POCl$_3$ (600 μL). After to mixture was heated to 65° C. for 20 minutes, it was cooled to room temperature and poured over ice to quench POCl$_3$. Upon neutralizing the ice mixture with saturated NaHCO$_3$ (6 mL), the bis-sulfonyl chloride crashes out of solution. After the product was then extracted with CH$_2$Cl$_2$ (3×20 mL), the combined organic phases were washed with brine (2×20 mL) and dried over sodium sulfate. Evaporation of the solvent provided the crude bis-sulfonyl chloride as a blue solid, which was used in the next reaction without further purification. ESI-MS calculated for $C_{24}H_{28}Cl_2N_3O_5S_2^+$: 572.1, observed: 572.1.

2,2,2-Trifluoro-1-(4-nitro-phenyl)-ethanol (39 mg, 0.18 mmol) was dissolved in anhydrous dichloromethane (1 mL). The mixture was cooled to 0° C. in an ice bath, followed by the addition of triethylamine (0.1 mL, 0.7 mmol). The bis-sulfonyl chloride product was dissolved in 4 mL $CH_2Cl_2$ and was added dropwise over 40 minutes to the alcohol solution above. The reaction mixture was then brought to room temperature and stirred overnight. The mixture was then diluted into 1 M HCl (50 mL) and was extracted with dichloromethane (3×50 mL). The combined organic phases were washed with brine (1×75 mL) and dried over sodium sulfate. Evaporation of the solvent under vacuum resulted in the crude product as a blue solid. The crude product was purified first by gravity chromatography (15% methanol/dichloromethane), and then by flash column chromatography (0-15% methanol/dichloromethane) to yield Compound 25 as a blue solid (0.28 mg, 2%). HR-EIMS m/z calculated for $C_{40}H_{38}F_6N_5O_{11}S_2$: 942.1913. found: 942.1936.

Example 14

Preparation of Compound 26

4-bromo-benzenesulfonic acid 2,2,2-trifluoro-1-p-tolyl-ethyl ester

4-Bromobenzenesulfonyl chloride (368 mg, 1.44 mmol) and 2,2,2-trifluoro-1-p-tolyl-ethanol (249 mg, 1.31 mmol) were dissolved in $CH_2Cl_2$ (1.62 mL). DABCO (176 mg, 1.57 mmol) dissolved in $CH_2Cl_2$ (1 mL) was added dropwise to the above mixture, resulting in precipitate formation. The mixture was then stirred for 4 hours at room temperature. The reaction was quenched by the addition of 1M NaOH (1 mL), resulting in elimination of the precipitate. The solution was diluted into ethyl acetate (150 mL) and extracted with saturated $NaHCO_3$ (3×75 mL), 0.1M HCl (3×75 mL), water (75 mL) and brine (75 mL). The organic phase was then dried over $Na_2SO_4$ and the solvent was removed via rotary evaporation to yield pure Compound 26 as a flaky, ivory solid (446 mg, 83%). $^1$H-NMR ($CDCl_3$): δ 7.58 (d, 2H, J=8.7 Hz), 7.54 (d, 2H, J=8.7 Hz), 7.18 (d, 2H, J=8.0 Hz), 7.11 (d, 2H, 8.0 Hz), 5.65 (q, 1H, $J_{HF}$=6.3 Hz), 2.36 (s, 3H). $^{19}$F-NMR ($CDCl_3$): δ −76.5 (d, J=6.3 Hz). $^{13}$C-NMR ($CDCl_3$): δ 141.1, 135.5, 132.6, 129.7, 129.6, 129.5, 128.4, 126.4, 122.4 (q, $^1J_{CF}$=281 Hz), 78.9 (q, $^2J_{CF}$=35 Hz), 21.5. HR-EIMS m/z calculated for $C_{15}H_{12}BrF_3O_3SNa$: 430.9540 and 432.9521. found: 430.9537 and 432.9521.

Example 15

Preparation of Compound 27

4-Iodo-benzenesulfonic acid 2,2,2-trifluoro-1-p-tolyl-ethyl ester

Compound 27 was prepared in a manner similar to that used to prepare Compound 26 described in Example 14 except that 4-bromobenzenesulfonyl chloride was replaced with 4-iodobenzenesulfonyl chloride. Compound 27 was obtained as a powdery, white solid (547 mg, 89%). $^1$H-NMR ($CDCl_3$): δ 7.76 (d, 2H, J=8.7 Hz), 7.42 (d, 2H, J=8.7 Hz), 7.17 (d, 2H, J=8.2 Hz), 7.11 (d, 2H, 8.0 Hz), 5.64 (q, 1H, $J_{HF}$=6.3 Hz), 2.36 (s, 3H). $^{19}$F-NMR ($CDCl_3$): δ −76.5 (d, J=6.3 Hz). $^{13}$C-NMR ($CDCl_3$): δ 141.1, 138.5, 136.1, 129.7, 129.3, 128.4, 126.3, 122.4 (q, $^1J_{CF}$=281 Hz), 102.2, 78.9 (q, $^2J_{CF}$=35 Hz), 21.6. HR-EIMS m/z calculated for $C_{15}H_{12}F_3IO_3SNa$: 478.9402. found: 478.9389.

Example 16

Preparation of Compound 28

5-Dimethylamino-naphthalene-1-sulfonic acid 1-(4-ethoxycarbonyloxy-phenyl)-2,2,2-trifluoro-ethyl ester

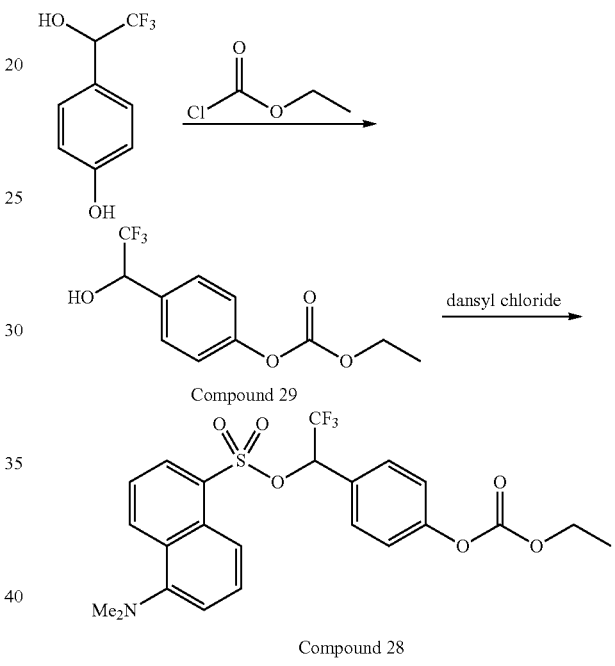

Compound 29

4-(2,2,2-Trifluoro-1-hydroxy-ethyl)-phenol (300 mg, 1.56 mmol) was dissolved in THF (9 mL) and cooled to 0° C. in an ice bath. After triethylamine (0.24 mL, 1.72 mmol) was added to the solution, the reaction was stirred for 10 minutes. Ethyl chloroformate (0.16 mL, 1.72 mmol) dissolved in THF (1 mL) was added dropwise via syringe to the reaction flask. Upon completion of dropwise addition, the reaction was brought to room temperature and stirred for 3 hours. After the solvent was removed via rotary evaporation, the residue was taken up in 0.1 M hydrochloric acid (80 mL). The product was extracted with ethyl acetate (6×20 mL) and the combined organic phases were washed with brine (60 mL) and dried over sodium sulfate. Removal of the solvent under vacuum resulted in a clear liquid. The crude product was purified by flash column chromatography (0-30% ethyl acetate/hexanes) to yield Compound 29 as a white solid (305 mg, 74%). $^1$H-NMR ($CD_3OD$): δ 7.53 (d, 2H, J=8.8 Hz), 7.21 (d, 2H, J=8.8 Hz), 5.05 (q, 1H, $J_{HF}$=7.1 Hz), 4.28 (q, 2H, J=7.1 Hz), 1.34 (t, 3H, J=7.1 Hz). $^{19}$F-NMR ($CD_3OD$): δ −80.2 (d, J=7.0 Hz). $^{13}$C-NMR ($CD_3OD$): δ 153.9, 151.9, 133.6, 128.8, 125

(q, $^1J_{CF}$=282 Hz), 120.9, 71.3 (q, $^2J_{CF}$=31 Hz), 64.8, 13.3. HR-EIMS m/z calculated for $C_{11}H_{12}F_3O_4$: 265.0688. found: 265.0667.

Compound 28

Dansyl chloride (116 mg, 0.43 mmol) and Compound 29 obtained above (104 mg, 0.394 mmol) were dissolved in $CH_2Cl_2$ (2 mL). DABCO (53 mg, 0.47 mmol) dissolved in $CH_2Cl_2$ (0.5 mL) was added dropwise to the above solution. The solution thus formed was stirred for 4 hours at room temperature. After the solvent was removed via rotary evaporation, pure Compound 28 was isolated by flash column chromatography (0-50% ethyl acetate/hexanes) as a greenish-yellow solid (188 mg, 96%). $^1$H-NMR (CD$_3$OD): δ 8.47 (d, 1H, J=8.5 Hz), 8.14 (d, 1H, J=8.7 Hz), 8.13 (dd, 1H, J=1.3 Hz, 7.4 Hz), 7.57 (dd, 1H, J=7.6 Hz, 8.7 Hz), 7.45 (dd, 1H, J=7.4 Hz, 8.6 Hz), 7.22 (dd, 1H, J=0.8 Hz, 7.6 Hz), 7.06 (d, 2H, J=8.7 Hz), 6.73 (d, 2H, J=8.8 Hz), 5.93 (q, 1H, $J_{HF}$=6.5 Hz), 4.23 (q, 2H, J=7.1 Hz), 2.81 (s, 6H), 1.32 (t, 3H, J=7.1 Hz). $^{19}$F-NMR (CD$_3$OD): δ −78.1 (d, J=6.5 Hz). $^{13}$C-NMR (CDCl$_3$): δ 153.1, 152.4, 151.9, 132.4, 131.6, 130.49, 130.46, 129.9, 129.7, 129.6, 129.1, 126.7, 122.9, 122.3 (q, $^1J_{CF}$=281 Hz), 120.9, 119.4, 115.8, 78.1 (q, $^2J_{CF}$=35 Hz), 65.2, 45.6, 14.4. HR-EIMS m/z calculated for $C_{23}H_{23}F_3NO_6S$: 498.1198. found: 498.1187.

Example 17

Preparation of Compound 30

1-[4-(2,2,2-Trifluoro-1-hydroxy-ethyl)-phenylsulfanyl]-pyrrolidine-2,5-dione

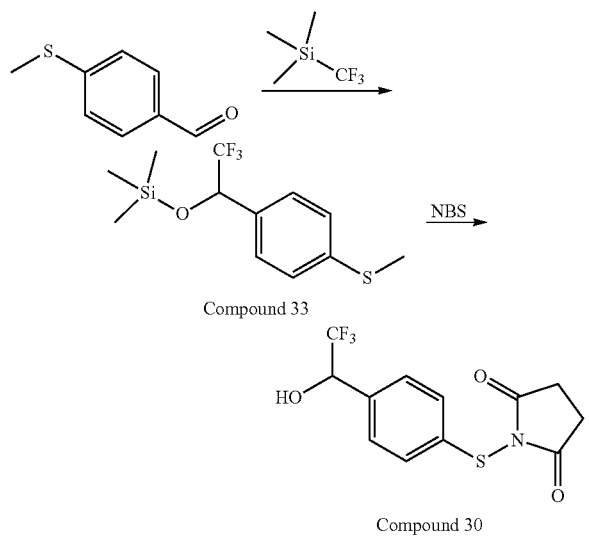

Compound 33

Compound 30

Trimethyl-[2,2,2-trifluoro-1-(4-methylsulfanyl-phenyl)-ethoxy]-silane (Compound 33)

4-Methylsulfanyl-benzaldehyde (2.4 g, 8.16 mmol) and trimethyl(trifluoromethyl)-silane (2.9 g, 19.4 mmol) were dissolved in anhydrous THF (20 mL) under argon gas at 0° C. TBAF (20 drops) was added to this solution dropwise. The reaction was then raised to room temperature and stirred for 4 hours. Upon completion, THF from the reaction mixture was removed under reduced pressure. The crude material was purified with silica-gel flash chromatography using neat dichloromethane to yield Compound 33 as a yellow oil (4.6 g, 96%). $^1$H-NMR (CDCl$_3$): δ 7.35 (d, 2H J=8.29 Hz), 7.24 (d, 2H, J=8.54 Hz), 4.86 (q, 1H, $J_{HF}$=6.56 Hz), 2.41 (s, 3H), 0.11 (s, 7H). $^{19}$F-NMR (CDCl$_3$): δ −78.97 (d, 6.57 Hz). HR-EIMS m/z calculated for $C_{12}H_{18}F_3OSSi$: 295.0800. found: 295.0797.

Trimethyl-[2,2,2-trifluoro-1-(4-methylsulfanyl-phenyl)-ethoxy]-silane (5 g, 17 mmol) and N-Bromosuccinimide (4.55 g, 25.5 mmol) were dissolved in anhydrous dichloromethane (35 mL) under argon gas and at room temperature. The reaction was stirred for 24 hours under argon. Upon completion, dichloromethane was removed under reduced pressure. The crude material was then purified with neat dichloromethane to give a yellow oil. The resulting oil was stirred in 1:1 1M HCL/THF (300 mL) for 3 hours. The final product was extracted with ethyl acetate (3×200 mL). The combined organic layers were first washed with water (3×200 mL), followed by brine (200 mL), and then dried over Na$_2$SO$_4$. The removal of organic solvent under reduced pressure gave Compound 30 as a white solid (3 g, 75% yield). $^1$H-NMR (CDCl$_3$): δ 7.62 (d, 2H J=8.54 Hz), 7.46 (d, 2H, J=8.08 Hz), 5.03 (q, 1H, $J_{HF}$=6.54 Hz), 2.86 (s, 4H). $^{19}$F-NMR (CDCl$_3$): δ −78.74 (d, 6.60 Hz).

Example 18

Preparation of Compound 31

3-Chloro-propane-1-sulfonic acid 2,2,2-trifluoro-1-(4-nitro-phenyl)-ethyl ester 2,2,2-Trifluoro-1-(4-nitro-phenyl)-ethanol (508 mg, 2.3 mmol) was dissolved in anhydrous dichloromethane (21 mL). The solution was cooled to 0° C. in an ice bath. Triethylamine (0.7 mL, 5 mmol) was then added to the solution. 3-Chloro-propane-sulfonyl chloride (0.4 mL, 3.3 mmol) dissolved in anhydrous dichloromethane (2.5 mL) was added dropwise via syringe to the above solution at a rate of 10 drops/minute. Upon completion of dropwise addition, the reaction was brought to room temperature and stirred overnight. The reaction was poured into 1 M hydrochloric acid (150 mL) and the product was extracted with dichloromethane (1×150 mL, 2×75 mL). The combined organic phases were washed with saturated sodium bicarbonate (2×100 mL), water (100 mL), and brine (100 mL), and dried over sodium sulfate. Removal of the solvent under vacuum provided pure Compound 31 as a gold oil (820 mg, 99%). $^1$H-NMR (CDCl$_3$): δ 8.33 (d, 2H, J=8.9 Hz), 7.71 (d, 2H, J=8.7 Hz), 5.90 (q, 1H, $J_{HF}$=6.1 Hz), 3.68 (t, 2H, J=6.3 Hz), 3.42 (t, 2H, J=7.4 Hz), 2.39-2.32 (m, 2H). $^{19}$F-NMR (CDCl$_3$): δ −76.1 (d, J=6.1 Hz).

Example 19

Preparation of Compound 32

3-Chloro-propane-1-sulfonic acid 2,2,2-trifluoro-1-(4-methyldisulfanyl-phenyl)-ethyl ester 2,2,2-Trifluoro-1-(4-methyldisulfanyl-phenyl)-ethanol (28 mg, 0.11 mmol) was dissolved in anhydrous dichloromethane (2.5 mL). The solution was cooled to 0° C. in an ice bath. Triethylamine (31 μL, 0.22 mmol) was then added to the solution. 3-Chloro-propanesulfonyl chloride (20 μL, 0.16 mmol) dissolved in anhydrous dichloromethane (0.5 mL) was added dropwise via syringe to the above solution at a rate of 10 drops/minute. Upon completion of dropwise addition, the reaction was brought to room temperature and stirred for 4 hours. The reaction mixture was poured into 1 M hydrochloric acid (40 mL) and the product was extracted with dichloromethane (1×60 mL, 2×20 mL). The combined organic phases were washed with saturated sodium bicarbonate (50 mL), water (40 mL), and brine (80 mL), and dried over sodium sulfate. After the solvent was removed via rotary evaporation, pure Compound 32 was isolated by flash column chromatography (0-20% ethyl acetate/hexanes) as a colorless oil (17 mg, 39%). $^1$H-NMR (CDCl$_3$): δ 7.61 (d, 2H, J=8.6 Hz), 7.46 (d, 2H, J=8.6 Hz), 5.77 (q, 1H, J$_{HF}$=6.3 Hz), 3.62 (t, 2H, J=6.1 Hz), 3.3-3.25 (m, 2H), 2.46 (s, 3H), 2.32-2.25 (m, 2H). $^{19}$F-NMR (CDCl$_3$): δ −76.3 (d, J=6.3 Hz).

Example 20

Preparation of Compound 34

2-(7-{1,1-Dimethyl-3-[4-(2,2,2-trifluoro-1-phenyl-ethoxysulfonyl)-butyl]-1,3-dihydro-benzo[e]indol-2-ylidene}-hepta-1,3,5-trienyl)-1,1-dimethyl-3-[4-(2,2,2-trifluoro-1-phenyl-ethoxysulfonyl)-butyl]-1H-benzo[e]indolium chloride Indocyanine green (sodium 4-[2-[(1E,3E,5E,7E)-7-[1,1-dimethyl-3-(4-sulfonatobutyl)benzo[e]indol-2-ylidene] hepta-1,3,5-trienyl]-1,1-dimethylbenzo[e]indol-3-ium-3-yl] butane-1-sulfonate, 22 mg, 28 µmol) was suspended in POCl$_3$ (0.3 mL). Following the addition of PCl$_5$ (12 mg, 58 µmol), the reaction mixture was stirred at room temperature overnight. The reaction mixture was then poured over ice to quench POCl$_3$ and the ice mixture was neutralized with saturated NaHCO$_3$ (8 mL) causing the bis-sulfonyl chloride to crash out of the solution. After the mixture was then extracted with CH$_2$Cl$_2$ (1×125 mL, 1×50 mL), the combined organic phases were washed with brine (1×50 mL) and dried over sodium sulfate. Evaporation of the solvent provided the crude product, a green solid, which was identified by LC-MS as the bis-sulfonyl chloride. The crude product was used in the next step without further purification. LC-MS calculated for C$_{43}$H$_{47}$Cl$_2$N$_2$O$_4$S$_2^+$: 789.23, observed: 789.3.

2,2,2-Trifluoro-1-phenyl-ethanol (19 µL, 0.14 mmol) was dissolved in anhydrous dichloromethane (0.4 mL) and cooled to 0° C. in an ice bath. Triethylamine (39 µL, 0.28 mmol) was then added to the alcohol solution. The bis-sulfonyl chloride product obtained above was dissolved in CH$_2$Cl$_2$ (1 mL) and added dropwise over 20 minutes to the alcohol solution. The reaction mixture was stirred at 0° C. for 1 hour and then diluted into 1 M HCl (40 mL). After the mixture thus formed was extracted with dichloromethane (3×30 mL), the combined organic phases were washed with brine (1×50 mL) and dried over sodium sulfate. Evaporation of the solvent under vacuum resulted in the crude product as a green solid. The crude product was purified by flash column chromatography (0-10% methanol/dichloromethane) to yield Compound 34 as a green solid (6.1 mg, 19%). HR-EIMS m/z calculated for C$_{59}$H$_{59}$F$_6$N$_2$O$_6$S$_2$: 1069.3718. found: 1069.3749.

Example 21

Preparation of Compound 35

2-[7-(1,1-Dimethyl-3-{4-[2,2,2-trifluoro-1-(4-acetoxy-phenyl)-ethoxysulfonyl]-butyl}-1,3-dihydro-benzo[e]indol-2-ylidene)-hepta-1,3,5-trienyl]-1,1-dimethyl-3-{4-[2,2,2-trifluoro-1-(4-acetoxy-phenyl)-ethoxysulfonyl]-butyl}-1H-benzo[e]indolium chloride Indocyanine green (sodium 4-[2-[(1E,3E,5E,7E)-7-[1,1-dimethyl-3-(4-sulfonatobutyl)benzo[e]indol-2-ylidene] hepta-1,3,5-trienyl]-1,1-dimethylbenzo[e]indol-3-ium-3-yl] butane-1-sulfonate, 70 mg, 90 µmol) was suspended in POCl$_3$ (1 mL) and heated to 65° C. for 20 minutes. After the reaction mixture was cooled to room temperature, it was poured over ice to quench POCl$_3$ and neutralized with saturated NaHCO$_3$ (20 mL). The product, which had crashed out of the solution upon neutralization, was dissolved in CH$_2$Cl$_2$ (100 mL) and separated from the aqueous phase. The aqueous phase was further extracted with CH$_2$Cl$_2$ (4×50 mL). The combined organic phases were washed with brine (2×100 mL) and dried over sodium sulfate. Evaporation of the solvent provided the crude product, a green solid, which was identified as the bis-sulfonyl chloride by LC-MS. The crude product was used in the next step without further purification. LC-MS calculated for C$_{43}$H$_{47}$Cl$_2$N$_2$O$_4$S$_2^+$: 789.23, observed: 789.3.

Acetic acid 4-(2,2,2-trifluoro-1-hydroxy-ethyl)-phenyl ester (106 mg, 0.45 mmol) was dissolved in anhydrous dichloromethane (3 mL) and cooled to 0° C. in an ice bath followed by the addition of triethylamine (0.63 mL, 4.5 mmol. The bis-sulfonyl chloride product obtained above was dissolved in 5 mL CH$_2$Cl$_2$ and added dropwise over 30 minutes to the alcohol solution. The reaction mixture was stirred at 0° C. for 1 hour and then diluted into 1 M HCl (150 mL). The mixture was extracted with dichloromethane (1×150 mL, 3×50 mL). The combined organic phases were washed with brine (150 mL) and dried over sodium sulfate. Evaporation of the solvent under vacuum resulted in the crude product as a green solid. The crude material was purified twice by flash column chromatography (0-15% methanol/dichloromethane) to yield the product as a green solid (14 mg, 13%). HR-EIMS m/z calculated for C$_{63}$H$_{63}$F$_6$N$_2$O$_{10}$S$_2$: 1185.3828. found: 1185.3833.

Example 22

Cleavage of Reductive-Labile Protecting Group in Compound 1

Compound 1 was treated with 1 mM of a reducing agent, i.e., dithiothreitol or tris(2-carboxyethyl)phosphine, for 30 minutes at room temperature in water (pH 7). The solution was analyzed by TLC. A control experiment was conducted by analyzing an aqueous solution containing Compound 1 without being treated with a reducing agent by using TLC. The results suggested that the protecting group in Compound 1 (i.e.,

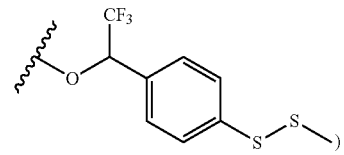 [SMILES: *OC(c1ccc(SSC)cc1)C(F)(F)F]

was rapidly cleaved to form a deprotected sulfonate dye.

Other embodiments are within the scope of the following claims.

What is claimed is:
1. A compound, comprising:
a fluorophore covalently bonded to at least one protected sulfonate group of formula (I):

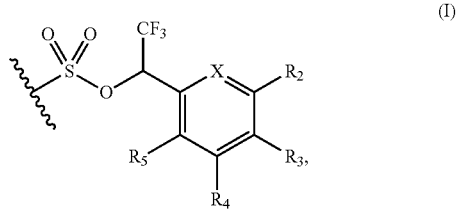

wherein
  X is C(R$_1$) or N, in which R$_1$ is H, halo, or C$_1$-C$_{10}$ alkyl;
  R$_3$ is S—S—R$_a$, S—R$_a$, NO$_2$, OR$_a$, OC(O)R$_a$, halo C$_1$-C$_{10}$ alkyl, or aryl, in which R$_a$ is C$_1$-C$_{10}$ alkoxy, C$_1$-C$_{10}$ alkyl, or C$_1$-C$_{20}$ heterocycloalkyl and is optionally substituted with NRR', halo, OR, C$_3$-C$_{20}$ cycloalkyl, C$_1$-C$_{20}$ heterocycloalkyl, aryl, or heteroaryl, each of R and R', independently, being H or C$_1$-C$_{10}$ alkyl; and
  each of R$_2$, R$_4$, and R$_5$, independently, is H, halo, or C$_1$-C$_{10}$ alkyl;
  provided that, when X is CH, R$_3$ is not OC(O)CH$_3$.

2. The compound of claim 1, wherein R$_3$ is S—S—R$_a$ or NO$_2$, in which R$_a$ is C$_1$-C$_{10}$ alkyl optionally substituted with NRR', each of R and R', independently, being H or C$_1$-C$_{10}$ alkyl.

3. The compound of claim 2, wherein R$_3$ is S—S—R$_a$, in which R$_a$ is CH$_3$ or CH$_2$CH$_2$N(CH$_3$)$_2$.

4. The compound of claim 3, wherein X is C(R$_1$), in which R$_1$ is H or F.

5. The compound of claim 4, wherein each of R$_2$, R$_4$, and R$_5$ is H.

6. The compound of claim 1, wherein R$_3$ is halo C$_1$-C$_{10}$ alkyl, or aryl.

7. The compound of claim 6, wherein R$_3$ is F methyl, isopropyl, or phenyl.

8. The compound of claim 7, wherein X is C(R$_1$), in which R$_1$ is H or F.

9. The compound of claim 8, wherein R$_5$ is H or F and each of R$_2$ and R$_4$ is H.

10. The compound of claim 1, wherein R$_3$ is OC(O)R$_a$, in which R$_a$ is C$_1$-C$_{10}$ alkyl optionally substituted with halo, OR, C$_3$-C$_{20}$ cycloalkyl, C$_1$-C$_{20}$ heterocycloalkyl, aryl, or heteroaryl, R being H or C$_1$-C$_{10}$ alkyl.

11. The compound of claim 10, wherein R$_3$ is OC(O)R$_a$, in which R$_a$ is methyl optionally substituted with Cl, Br, OCH$_3$, or

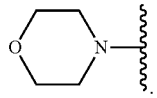

12. The compound of claim 11, wherein X is C(R$_1$) or N, in which R$_1$ is H.

13. The compound of claim 12, wherein each of R$_2$, R$_4$, and R$_5$ is H.

14. The compound of claim 1, wherein the fluorophore comprises a naphthalene moiety, a cyanine moiety, an oxazine moiety, a coumarin moiety, a rhodamine moiety, or a xanthene moiety, each of which is optionally substituted with C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, heteroaryl, OR$_b$, SR$_b$, NR$_b$R$_c$, COOR$_b$, or COR$_b$, each R$_b$ and R$_c$, independently, being H or C$_1$-C$_{10}$ alkyl.

15. The compound of claim 14, wherein the fluorophore comprises a moiety selected from the group consisting of:

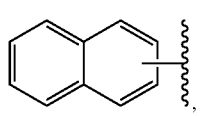 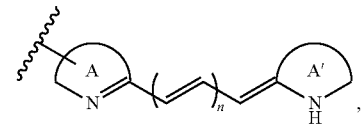

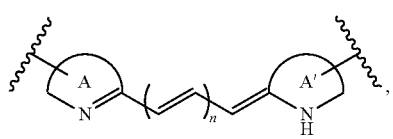

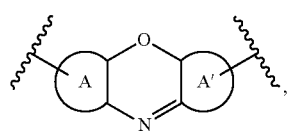 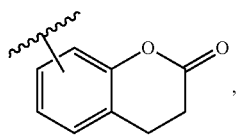

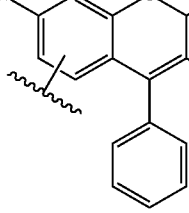

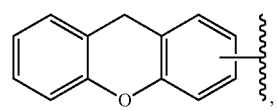

in which n is 1, 2, or 3, each of A and A', independently, is a 5-7 membered ring optionally fused with at least one 5-7 membered ring, and each moiety is optionally substituted with C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, heteroaryl, OR$_b$, SR$_b$, NR$_b$R$_c$, COOR$_b$, or COR$_b$, each R$_b$ and R$_c$, independently, being H or C$_1$-C$_{10}$ alkyl.

16. The compound of claim 15, wherein the fluorophore is

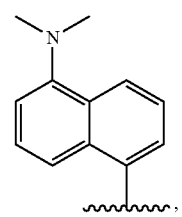

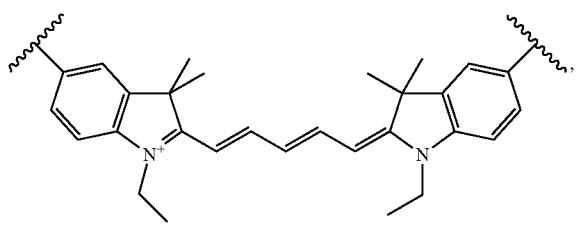

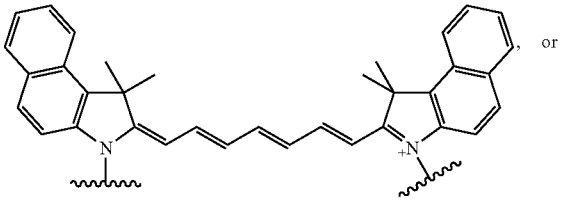

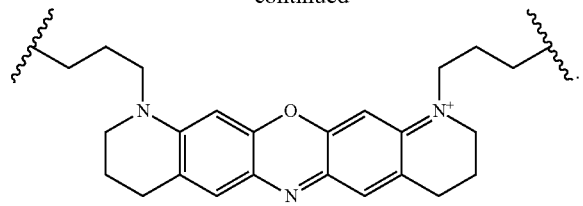

17. An imaging method, comprising:
    delivering a compound of claim 1 into a cell; and
    irradiating the cell with an excitation light, thereby generating fluorescence from the cell.

18. The method of claim 17, wherein the fluorescence has a wavelength greater than about 600 nm.

19. A compound, comprising:
    a fluorophore covalently bonded to at least one protected sulfonate group of formula (I):

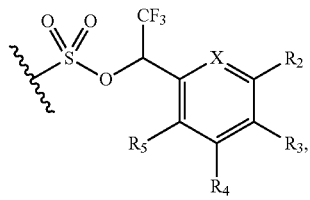

(I)

wherein
  X is $C(R_1)$ or N, in which $R_1$ is H, halo, or $C_1$-$C_{10}$ alkyl;
  $R_3$ is H, S—S—$R_a$, S—$R_a$, $NO_2$, $OR_a$, $OC(O)R_a$, halo, $C_1$-$C_{10}$ alkyl, or aryl, in which $R_a$ is $C_1$-$C_{10}$ alkoxy, $C_1$-$C_{10}$ alkyl, or $C_1$-$C_{20}$ heterocycloalkyl and is optionally substituted with NRR', halo, OR, $C_3$-$C_{20}$ cycloalkyl, $C_1$-$C_{20}$ heterocycloalkyl, aryl, or heteroaryl, each of R and R', independently, being H or $C_1$-$C_{10}$ alkyl;
  each of $R_2$, $R_4$, and $R_5$, independently, is H, halo, or $C_1$-$C_{10}$ alkyl; and
  the fluorophore comprises a cyanine moiety, an oxazine moiety, a coumarin moiety, a rhodamine moiety, or a xanthene moiety, each of which is optionally substituted with $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, $OR_b$, $SR_b$, $NR_bR_c$, $COOR_b$, or $COR_b$, each $R_b$ and $R_c$, independently, being H or $C_1$-$C_{10}$ alkyl;
  provided that, when X is CH, $R_3$ is not $OC(O)CH_3$.

20. The compound of claim 19, wherein the fluorophore comprises a moiety selected from the group consisting of:

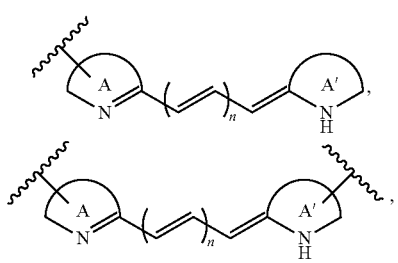

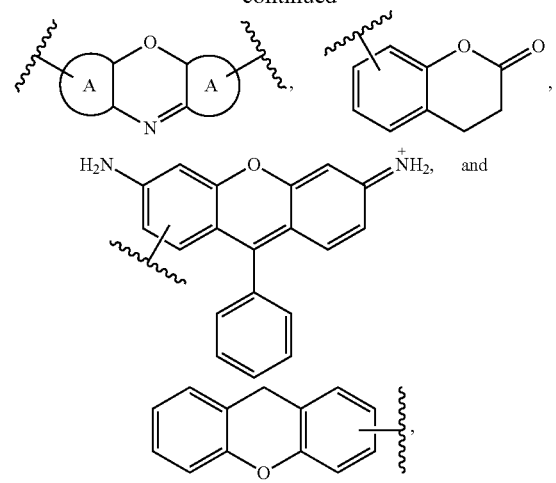

in which n is 1, 2, or 3, each of A and A', independently, is a 5-7 membered ring optionally fused with at least one 5-7 membered ring, and each moiety is optionally substituted with $C_1$-$C_{10}$ alkyl, $C_2$-$C_{10}$ alkenyl, $C_2$-$C_{10}$ alkynyl, $C_3$-$C_{20}$ cycloalkyl, $C_{20}$ cycloalkenyl, $C_1$-$C_{20}$ heterocycloalkyl, $C_1$-$C_{20}$ heterocycloalkenyl, aryl, heteroaryl, $OR_b$, $SR_b$, $NR_bR_c$, $COOR_b$, or $COR_b$, each $R_b$ and $R_c$, independently, being H or $C_1$-$C_{10}$ alkyl.

21. The compound of claim 20, wherein the fluorophore is

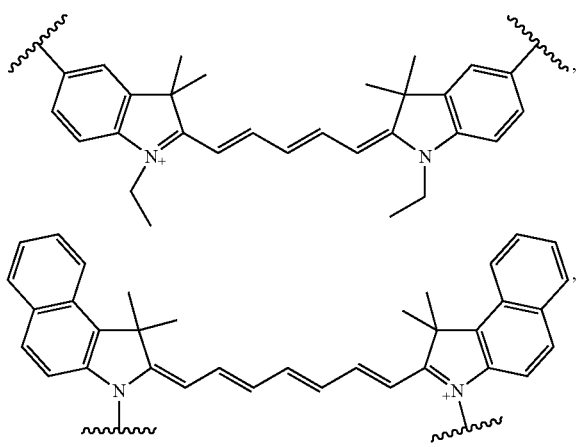

or

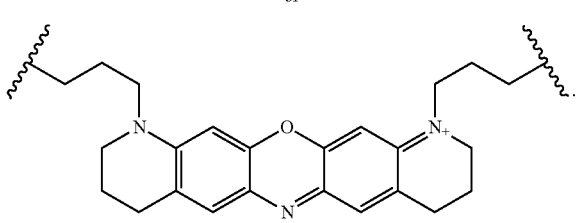

22. The compound of claim 19, wherein $R_3$ is H.

23. The compound of claim 19, wherein X is $C(R_1)$, in which $R_1$ is H or F.

24. The compound of claim 19, wherein each of $R_2$, $R_4$, and $R_5$, independently, is H or F.

* * * * *

UNITED STATES PATENT AND TRADEMARK OFFICE
CERTIFICATE OF CORRECTION

PATENT NO. : 9,329,185 B2
APPLICATION NO. : 14/202211
DATED : May 3, 2016
INVENTOR(S) : Stephen C. Miller, Steven M. Pauff and Adam Choi Page 1 of 1

It is certified that error appears in the above-identified patent and that said Letters Patent is hereby corrected as shown below:

In the claims

Column 42, line 25, claim 20, delete "$C_{20}$ cycloalkenyl," and insert -- $C_3$-$C_{20}$ cycloalkenyl, --.

Signed and Sealed this
Twenty-first Day of June, 2016

Michelle K. Lee
*Director of the United States Patent and Trademark Office*